US011224503B2

(12) United States Patent
Karavany et al.

(10) Patent No.: US 11,224,503 B2
(45) Date of Patent: Jan. 18, 2022

(54) AORTIC IMPLANT

(71) Applicant: Hemodynamx-Techologies Ltd., Modiin (IL)

(72) Inventors: Sagy Karavany, Kibbutz Dvir (IL); Tanhum Feld, Moshav Merhavya (IL); Boaz Nishri, D.N. Menashe (IL); Menashe Yacoby, Shoham (IL)

(73) Assignee: Hemodynamx-Techologies Ltd., Modiin (IL)

( * ) Notice: Subject to any disclaimer, the term of this patent is extended or adjusted under 35 U.S.C. 154(b) by 240 days.

(21) Appl. No.: 16/322,047

(22) PCT Filed: Aug. 10, 2017

(86) PCT No.: PCT/IL2017/050884
§ 371 (c)(1),
(2) Date: Jan. 30, 2019

(87) PCT Pub. No.: WO2018/029688
PCT Pub. Date: Feb. 15, 2018

(65) Prior Publication Data
US 2019/0183629 A1    Jun. 20, 2019

Related U.S. Application Data

(60) Provisional application No. 62/373,993, filed on Aug. 12, 2016.

(51) Int. Cl.
*A61F 2/06*     (2013.01)
*A61F 2/966*    (2013.01)
*A61F 2/915*    (2013.01)

(52) U.S. Cl.
CPC .............. *A61F 2/06* (2013.01); *A61F 2/966* (2013.01); *A61F 2002/068* (2013.01);
(Continued)

(58) Field of Classification Search
CPC ........ A61F 2/06; A61F 2002/068; A61F 2/07; A61F 2/966; A61F 2002/91525; A61F 2250/0039; A61F 2/2418; A61F 2/848
See application file for complete search history.

(56) References Cited

U.S. PATENT DOCUMENTS 5,139,515 A    8/1992  Robicsek
6,120,534 A *  9/2000  Ruiz ................. A61B 17/12109
                                                              606/194
(Continued)

FOREIGN PATENT DOCUMENTS

CN    101287424 A    10/2008
EP      1849440 A1   10/2007
(Continued)

OTHER PUBLICATIONS

Examination Report for Indian Application No. 201717029373 dated Oct. 8, 2020.
(Continued)

*Primary Examiner* — Tuan V Nguyen
(74) *Attorney, Agent, or Firm* — Marcus S. Simon

(57) ABSTRACT

Apparatus and methods are described including inserting an implantable device (20) into a blood vessel of a subject while the implantable device is disposed inside a delivery device and is constrained in a constrained configuration by the delivery device. The implantable device is released from the delivery device into the blood vessel, thereby causing the implantable device to assume a non-constrained configuration by an upstream end of the implantable device radially expanding (120), a central portion (122) of the implantable device radially expanding such that along the central portion of the implantable device the inner surface (24) of the implantable device defines a diverging portion (25) of a conduit (26), and the implantable device forming a folded portion (128) between the upstream end of the implantable
(Continued)

device and the central portion of the implantable device. Other applications are also described.

22 Claims, 11 Drawing Sheets

(52) U.S. Cl.
CPC .............. *A61F 2002/91525* (2013.01); *A61F 2230/0093* (2013.01); *A61F 2250/0039* (2013.01)

(56) References Cited

U.S. PATENT DOCUMENTS

| | | | |
|---|---|---|---|
| 7,018,404 | B2 | 3/2006 | Holmberg et al. |
| 7,766,814 | B2 | 8/2010 | Walsh |
| 8,585,572 | B2 | 11/2013 | Mehmanesh |
| 8,623,065 | B2 | 1/2014 | Lau et al. |
| 8,715,337 | B2 | 5/2014 | Chuter |
| 9,232,992 | B2 | 1/2016 | Heidner et al. |
| 10,368,985 | B2 | 8/2019 | Wilson et al. |
| 10,568,731 | B2 | 2/2020 | Karavany et al. |
| 2003/0045828 | A1 | 3/2003 | Wilk |
| 2004/0093058 | A1 | 5/2004 | Cottone et al. |
| 2004/0249439 | A1* | 12/2004 | Richter ............... A61F 2/958 623/1.15 |
| 2004/0260389 | A1 | 12/2004 | Case et al. |
| 2005/0222674 | A1 | 10/2005 | Paine |
| 2006/0009835 | A1 | 1/2006 | Osborne et al. |
| 2006/0106449 | A1* | 5/2006 | Ben Muvhar .... A61B 17/12172 623/1.15 |
| 2006/0149360 | A1 | 7/2006 | Schwammenthal et al. |
| 2006/0259134 | A1* | 11/2006 | Schwammenthal ...... A61F 2/24 623/2.11 |
| 2007/0185565 | A1* | 8/2007 | Schwammenthal .. A61F 2/2418 623/1.24 |
| 2007/0293808 | A1 | 12/2007 | Williams et al. |
| 2008/0071361 | A1 | 3/2008 | Tuval et al. |
| 2008/0071363 | A1 | 3/2008 | Tuval et al. |
| 2009/0105805 | A1 | 4/2009 | Baker et al. |
| 2009/0210047 | A1 | 8/2009 | Amplatz et al. |
| 2009/0222078 | A1 | 9/2009 | Greenberg |
| 2009/0240320 | A1 | 9/2009 | Tuval et al. |
| 2009/0270965 | A1 | 10/2009 | Sinha et al. |
| 2010/0023046 | A1* | 1/2010 | Heidner ........... A61B 17/12036 606/191 |
| 2010/0145433 | A1 | 6/2010 | Anukhin et al. |
| 2011/0288634 | A1 | 11/2011 | Tuval et al. |
| 2012/0010690 | A1 | 1/2012 | Richter et al. |
| 2012/0022629 | A1 | 1/2012 | Perera et al. |
| 2013/0013053 | A1 | 1/2013 | Hartley et al. |
| 2013/0144383 | A1 | 6/2013 | Thill et al. |
| 2013/0178750 | A1 | 7/2013 | Sheehan et al. |
| 2014/0257474 | A1* | 9/2014 | Roeder ................ A61F 2/2412 623/2.17 |
| 2015/0238315 | A1 | 8/2015 | Rabito et al. |
| 2015/0366693 | A1 | 12/2015 | Kagan et al. |
| 2017/0042551 | A1* | 2/2017 | Celermajer ............... A61F 2/07 |
| 2018/0036109 | A1 | 2/2018 | Karavany et al. |
| 2018/0353281 | A1* | 12/2018 | Nussinovitch ........... A61F 2/07 |
| 2019/0183629 | A1 | 6/2019 | Karavany et al. |

FOREIGN PATENT DOCUMENTS

| | | |
|---|---|---|
| EP | 2777618 A1 | 9/2014 |
| EP | 2896387 A1 | 7/2015 |
| EP | 2785277 B1 | 4/2017 |
| JP | 2001527453 A | 12/2001 |
| JP | 2008537891 A | 12/2005 |
| JP | 2007526789 A | 9/2007 |
| JP | 2011502628 A | 1/2011 |
| WO | 9852476 A1 | 11/1998 |
| WO | 03028522 A2 | 4/2003 |
| WO | 2005002466 A2 | 1/2005 |
| WO | 2005084730 A1 | 9/2005 |
| WO | 2006070372 A2 | 12/2005 |
| WO | 2006080010 A2 | 8/2006 |
| WO | 2009061419 A1 | 11/2008 |
| WO | 2012018590 A1 | 2/2012 |
| WO | 2015013344 A2 | 1/2015 |
| WO | 2016128983 A1 | 8/2016 |
| WO | 2018029688 A1 | 2/2018 |
| WO | 2018220589 A1 | 12/2018 |
| WO | 2019097424 A2 | 5/2019 |
| WO | 2020234787 A1 | 11/2020 |

OTHER PUBLICATIONS

International Search Report and Written Opinion from International Application No. PCT/IB2020/054761 dated Aug. 18, 2020.
Issue Notification for U.S. Appl. No. 15/550,661 dated Feb. 5, 2020.
Office Action for Chinese Application No. 201780049360.2 dated Oct. 10, 2020.
U.S. Appl. No. 16/322,047, filed Jan. 30, 2019.
U.S. Appl. No. 16/763,884, filed May 13, 2020.
U.S. Appl. No. 62/586,258, filed Nov. 15, 2017.
U.S. Appl. No. 62/630,406, filed Feb. 14, 2018.
European Search Report for European Application No. 16748842.8 dated Sep. 19, 2018.
Protege webpage—downloaded Mar. 19, 2015.
Chinese Office Action for Chinese Application No. 201680015323.5 dated Dec. 14, 2018.
International Search Report and Written Opinion from International Application No. PCT/IL2016/050170 dated Jun. 10, 2016.
International Search Report and Written Opinion from International Application No. PCT/IL2017/050884 dated Oct. 30, 2017.
Restriction Requirement for U.S. Appl. No. 15/550,661 dated Dec. 4, 2018.
U.S. Appl. No. 62/115,207, filed Feb. 12, 2015.
U.S. Appl. No. 62/265,571, filed Dec. 10, 2015.
U.S. Appl. No. 62/373,993, filed Aug. 12, 2016.
Heinrich, et al., "Experimental analysis of fluid mechanical energy Tosses in aortic valve stenosis: importance of pressure recovery", Annals of biomedical engineering, 24.6, 1996, pp. 685-694.
Non-Final Office Action for U.S. Appl. No. 15/550,661 dated Aug. 6, 2019.
Notice of Allowance for U.S. Appl. No. 15/550,661 dated Oct. 17, 2019.
Japanese Office Action for Japanese Application No. 2017-542883 dated Dec. 10, 2019.
U.S. Appl. No. 15/550,661, filed Aug. 11, 2017.
U.S. Appl. No. 16/743,721, filed Jan. 15, 2020.
Supplemental Notice of Allowability for U.S. Appl. No. 15/550,661 dated Jan. 23, 2020.
PCT, "International Search Report and Written Opinion", Application No. PCT/IB2018/058961, dated May 8, 2019, 25 pages.
USPTO, "Final Office Action", U.S. Appl. No. 15/550,661, filed Jun. 19, 2019, 10 pages.
USPTO, "Non-Final Office Action", U.S. Appl. No. 15/550,661, filed Feb. 20, 2019, 21 pages.
Notice of Allowance for U.S. Appl. No. 16/763,884 dated Aug. 16, 2021.
Office Action for Chinese Application No. 201780049360.2 dated May 25, 2021.
Office Action for Chinese Application No. 201910988467.4 dated May 24, 2021.
Extended European Search Report for European Application No. 18878693.3 dated Jul. 8, 2021.

* cited by examiner

AORTIC IMPLANT

CROSS-REFERENCE TO RELATED APPLICATIONS

The present application is the US national phase of International application PCT/IL2017/050884 to Karavany (published as WO 2018/029688), filed Aug. 10, 2017, which claims priority from U.S. Provisional Application 62/373,993 to Karavany, filed Aug. 12, 2016, entitled "Aortic implant."

The present application is related to International Application PCT/IL2016/050170 to Karavany, filed Feb. 11, 2016, which published as WO 16/128983, and which claims priority from:

U.S. Provisional Application 62/115,207 to Karavany, filed Feb. 12, 2015, entitled "Aortic implant," and U.S. Provisional Application 62/265,571 to Karavany, filed Dec. 10, 2015, entitled "Aortic implant."

All of the above-referenced applications are incorporated herein by reference.

FIELD OF EMBODIMENTS OF THE INVENTION

Some applications of the present invention generally relate to medical apparatus. Specifically, some applications of the present invention relate to an aortic implant and methods of use thereof.

BACKGROUND

Aortic valve stenosis is a common disease in which calcification of the cusps of the aortic valve cause the flexibility of the valve to be compromised and the open valve area to diminish. Once aortic valve stenosis develops, due to the reduction in the aortic valve diameter, blood flow is compromised. Aortic valve stenosis often progresses to heart failure and other life-threatening conditions.

SUMMARY OF EMBODIMENTS

For some applications of the present invention, a device is deployed inside a blood vessel of a subject. The device defines an inner surface that defines a conduit through the device that passes from the proximal end of the device to the distal end of the device. At least a portion of the conduit diverges in a direction from a proximal (i.e., upstream) end of the conduit to a distal (i.e., downstream) end of the conduit, such that the cross-sectional area of the conduit at its distal (i.e., downstream) end is greater than the cross-sectional area of the conduit at its proximal (i.e., upstream) end. The device is deployed within a longitudinal portion of the blood vessel, such that blood flow through the longitudinal portion of the blood vessel, via any flow path other than through the conduit, whether in the antegrade or retrograde direction, is less than 20 percent (e.g., less than 10 percent, or less than 5 percent) of the total blood flow through the longitudinal portion of the blood vessel. The divergence of the conduit is configured to reduce pressure loss of blood flowing through the conduit, relative to the loss of pressure of the blood flowing through the longitudinal portion of the blood vessel in the absence of the device. The divergence of the conduit is configured to reduce the blood pressure loss by reducing the area of flow separation.

The device is typically placed in the aorta (e.g., the ascending aorta) of a subject suffering from aortic valve stenosis, in the vicinity of the stenosed aortic valve. The blood exiting the subject's left ventricle is directed into the conduit and the conduit is shaped such as to reduce blood pressure loss by reducing the area of flow separation, as described hereinabove. Typically, by directing the blood to flow in the above-described manner, loss of pressure and energy of the blood flow exiting the left ventricle into the ascending aorta is reduced relative to loss of pressure and energy of the blood flow in the absence of the device. Thus, placement of the device in the subject's ascending aorta may decrease the subject's left ventricular pressure, reduce afterload, and/or and improve the subject's cardiac output. For some applications, regulating the blood flow from the aortic valve in the above-described manner may postpone or stop the degradation process leading to further aortic valve stenosis. An unhealthy flow regime in the ascending aorta can cause sequential deposits of thrombi on the valve surface that can cause further valve thickening, deformation and calcification leading to severe stenosis. The deployed device, by changing the flow regime, may reduce the inflammatory process that causes calcification. Thus, the device may decrease the degradation of the medical situation of the subject.

Typically, the circumference of a region at the distal end of the device apposes the wall of the blood vessel (e.g., the aorta) in which the device is placed. The device typically defines one or more surfaces that extend from the outside of the conduit to the inner wall of the blood vessel, and/or to an outer support structure that is in contact with the inner wall of the blood vessel. Typically, the one or more surfaces extend radially outward, around the full circumference of the conduit, from the conduit at least to the radial location of the inner surface of the outer support structure (such that the surface extends to the inner surface of the blood vessel, and/or to the outer support structure). The surfaces are configured to impede backflow of blood around the outside of the conduit (e.g., the distal end of the conduit), in the manner described herein.

Typically, the device defines a proximal outer surface that surrounds a proximal portion of the conduit. For some applications, the device defines a distal outer surface that surrounds a distal portion of the conduit. Typically, the surfaces extend from the outside of the conduit to the inner wall of the blood vessel, and/or to an outer support structure that is in contact with the inner wall of the blood vessel. The proximal and distal outer surfaces are configured such that, when the device is deployed inside a longitudinal portion of the subject's aorta, the surfaces substantially impede blood flow through the longitudinal portion of the aorta, whether in the antegrade or the retrograde direction, via any flow path other than through the conduit defined by the inner surface of the device. For example, the proximal and distal surfaces may be configured such that, when the device is deployed inside the longitudinal portion of the subject's aorta, flow via flow paths other than through the conduit defined by the inner surface of the device is less than 20 percent (e.g., less than 10 percent, or less than 5 percent) of total blood flow through the longitudinal portion of the subject's aorta.

For some applications, the device does not define a separate distal outer surface. Rather, the distal end of the inner surface that defines the conduit extends to the inner surface of the blood vessel, or to the outer support structure, such that the distal end of the inner surface impedes the backflow of blood around the outside of the distal end of the conduit. In this manner, the distal end of the inner surface acts as the distal outer surface.

For some applications, the proximal and distal outer surfaces and/or the inner surface are impermeable and prevent blood from flowing back toward the aortic valve during systole (and/or during diastole), around the outside of the conduit. By preventing blood from flowing back toward the aortic valve during systole, the surfaces prevent loss of pressure and energy of the blood flow exiting the left ventricle into the ascending aorta relative to loss of pressure and energy of the blood flow in the absence of the device. For some applications, the surfaces are not impermeable, but have a permeability that is sufficiently low as to substantially impede blood from flowing through the longitudinal portion of the aorta, via any flow path other than through the conduit defined by the inner surface of the device, in the manner described hereinabove.

For some applications, the device is configured to promote coagulation of blood that is disposed within a region between the conduit and the inner wall of the aorta within the longitudinal portion of the aorta in which the device is placed, by substantially reducing blood flow through this region relative to in the absence of the device. Typically, the material that defines the proximal, distal, and/or inner surfaces is configured to prevent any thrombi that develop within the region from exiting the region and entering the subject's bloodstream. For some applications, by promoting the coagulation of blood within the region, the device causes blood entering the region to become coagulated, such that the region becomes filled with coagulated blood within a given time period of the device being placed within the aorta (e.g., within one week, one month, or three months of the device being placed within the aorta), such that the coagulated blood impedes (e.g., blocks) the flow of blood through the region. For some application, the blood that becomes coagulated within the region is blood that became trapped within the region immediately upon deployment of the device. Alternatively or additionally, blood enters the region subsequent to the device having been deployed, and the blood that subsequently enters the region becomes coagulated.

It is noted that, typically, the device does not include a prosthetic valve disposed within the conduit or at any other location within the device. The device typically performs all of the functions described herein without requiring the use of a prosthetic valve of any type.

The terms "proximal" and "distal" as used in the present application refer to the location of the respective elements in the aorta with respect to the aortic valve. That is, the term "proximal" refers to an element that is "upstream" and closer to the aortic valve, and the term "distal" refers to an element that is "downstream" and further from the aortic valve. Thus, the term "proximal" is used synonymously with the term "upstream" and the term "distal" is used synonymously with the term "downstream." In cases in which the device is placed in a different position within the subject's body, the terms "proximal" and "distal" are to be understood with respect to the direction of blood flow, a location that is relatively upstream being considered "proximal" and a location that is relatively downstream being considered "distal."

There is therefore provided, in accordance with some applications of the present invention, apparatus for use with a delivery device, including:
an implantable device having a proximal end and a distal end, the implantable device being configured:
to be inserted into a blood vessel of a subject while the implantable device is disposed inside the delivery device and is constrained in a constrained configuration by the delivery device,
to assume a non-constrained configuration inside the blood vessel by being released from the delivery device,
in its constrained configuration, to define a tube having an inner surface and an outer surface, and
to assume its non-constrained configuration, by:
the proximal end of the implantable device radially expanding such that a proximal portion of the outer surface of the implantable device contacts an inner wall of the blood vessel,
a central portion of the implantable device radially expanding such that along the central portion of the implantable device, the inner surface defines a diverging portion of a conduit, the conduit extending through the implantable device, and the diverging portion diverging in a direction from a proximal end of the conduit to a distal end of the conduit, such that a cross-sectional area of the diverging portion of the conduit at its distal end is greater than the cross-sectional area of the diverging portion of conduit at its proximal end,
the distal end of the implantable device radially expanding such that a distal portion of the outer surface contacts the inner wall of the blood vessel, and
the implantable device forming a folded portion between the proximal end of the implantable device and the central portion of the implantable device, such that along a longitudinal direction of the implantable device, there is partial overlap between the proximal portion of the outer surface of the implantable device and the central portion of the implantable device.

In some applications, the implantable device is configured to form the folded portion by forming a folded portion that has a sinusoidal cross-sectional shape.

In some applications, the implantable device does not include a prosthetic valve.

In some applications, the implantable device is configured such that, upon the implantable device assuming its non-constrained configuration within a longitudinal portion of an aorta of the subject, the implantable device reduces pressure loss within the aorta relative to pressure loss within the aorta in an absence of the implantable device.

In some applications, when in the non-constrained configuration inside the blood vessel, the implantable device is configured to define, at a region at its distal end, a surface extending radially outward, around a full circumference of the conduit, from the conduit to the inner wall of the blood vessel.

In some applications, the implantable device is made of a single continuous piece of stent graft material.

In some applications, the implantable device is configured such that, when the implantable device is in the non-constrained within the blood vessel, the diverging portion of the conduit has a length of more than 20 mm. In some applications, the implantable device is configured such that, when the implantable device is in the non-constrained within the blood vessel, the length of the diverging portion of the conduit is less than 70 mm.

In some applications, the implantable device is configured such that, when the implantable device is in the non-constrained configuration inside the blood vessel, a ratio between a diameter of the conduit at the distal end of the diverging portion of the conduit and a diameter of the conduit at the proximal end of the diverging portion of the conduit is less than 5:4. In some applications, the implantable device is configured such that, when the implantable device is in the non-constrained configuration inside the blood vessel, the ratio between the diameter of the conduit at the distal end of the diverging portion of the conduit and the diameter of the conduit at the proximal end of the diverging portion of the conduit is more than 7:6.

In some applications, when in the non-constrained configuration inside the blood vessel, the implantable device is configured to impede blood flow through a longitudinal portion of the blood vessel in which the implantable device is placed, via any flow path other than through the conduit, to less than 20 percent of total blood flow through the longitudinal portion of the blood vessel. In some applications, when in the non-constrained configuration inside the blood vessel, the implantable device is configured to impede blood flow through the longitudinal portion of the blood vessel in which the implantable device is placed such that there is no blood flow through the longitudinal portion of the blood vessel, via any flow path other than through the conduit.

There is further provided, in accordance with some applications of the present invention, a method including:
inserting an implantable device into a blood vessel of a subject while the implantable device is disposed inside a delivery device and is constrained in a constrained configuration by the delivery device, the implantable device defining a tube having an inner surface and an outer surface, while the implantable device is in its constrained configuration; and
releasing the implantable device from the delivery device into the blood vessel, thereby causing the implantable device to assume a non-constrained configuration by:
an upstream end of the implantable device radially expanding such that an upstream portion of the outer surface of the implantable device contacts an inner wall of the blood vessel,
a central portion of the implantable device radially expanding such that along the central portion of the implantable device, the inner surface defines a diverging portion of a conduit, the conduit extending through the implantable device, and the diverging portion diverging in a direction from an upstream end of the conduit to a downstream end of the conduit, such that a cross-sectional area of the diverging portion of the conduit at its downstream end is greater than the cross-sectional area of the diverging portion of the conduit at its upstream end,
a downstream end of the implantable device radially expanding such that a downstream portion of the outer surface contacts an inner wall of the blood vessel, and
the implantable device forming a folded portion between the upstream end of the implantable device and the central portion of the implantable device, such that along a longitudinal direction of the implantable device, there is partial overlap between the upstream portion of the outer surface of the implantable device and the central portion of the implantable device.

There is further provided, in accordance with some applications of the present invention, apparatus for use with a delivery device, including:
an implantable device having a proximal end and a distal end, the implantable device being configured:
to be inserted into a blood vessel of a subject while the implantable device is disposed inside the delivery device and is constrained in a constrained configuration by the delivery device,
to assume a non-constrained configuration inside the blood vessel by being released from the delivery device,
in its constrained configuration, to define a tube having an inner surface and an outer surface,
to assume its non-constrained configuration, by:
the inner surface at the proximal end of the device inverting and radially expanding such as to contact an inner wall of the blood vessel,
a central portion of the device radially expanding such that, along the central portion of the device, the inner surface defines a diverging portion of a conduit, the conduit extending through the implantable device, and the diverging portion diverging in a direction from a proximal end of the conduit to a distal end of the conduit, such that a cross-sectional area of the diverging portion of the conduit at its distal end is greater than the cross-sectional area of the diverging portion of the conduit at its proximal end, and
the distal end of the implantable device radially expanding such that a distal portion of the outer surface contacts the inner wall of the blood vessel.

In some applications, the implantable device does not include a prosthetic valve.

In some applications, the implantable device is configured such that, upon the implantable device assuming its non-constrained configuration within a longitudinal portion of an aorta of the subject, the implantable device reduces pressure loss within the aorta relative to pressure loss within the aorta in an absence of the implantable device.

In some applications, when in the non-constrained configuration inside the blood vessel, the implantable device is configured to define, at a region at its distal end, a surface extending radially outward, around a full circumference of the conduit, from the conduit to the inner wall of the blood vessel.

In some applications, the implantable device is made of a single continuous piece of stent graft material.

In some applications, the implantable device is configured such that, when the implantable device is in the non-constrained within the blood vessel, the diverging portion of the conduit has a length of more than 20 mm. In some applications, the implantable device is configured such that, when the implantable device is in the non-constrained within the blood vessel, the length of the diverging portion of the conduit is less than 70 mm.

In some applications, the implantable device is configured such that, when the implantable device is in the non-constrained configuration inside the blood vessel, a ratio between a diameter of the conduit at the distal end of the diverging portion of the conduit to a diameter of the conduit at the proximal end of the diverging portion of the conduit is less than 5:4. In some applications, the implantable device is configured such that, when the implantable device is in the non-constrained configuration inside the blood vessel, the ratio between the diameter of the conduit at the distal end of the diverging portion of the conduit to the diameter of the conduit at the proximal end of the diverging portion of the conduit is more than 7:6.

In some applications, when in the non-constrained configuration inside the blood vessel, the implantable device is configured to impede blood flow through a longitudinal portion of the blood vessel in which the implantable device is placed, via any flow path other than through the conduit, to less than 20 percent of total blood flow through the longitudinal portion of the blood vessel. In some applications, when in the non-constrained configuration inside the blood vessel, the implantable device is configured to impede blood flow through the longitudinal portion of the blood vessel in which the implantable device is placed such that there is no blood flow through the longitudinal portion of the blood vessel, via any flow path other than through the conduit.

There is further provided, in accordance with some applications of the present invention, a method including:

inserting an implantable device into a blood vessel of a subject while the implantable device is disposed inside a delivery device and is constrained in a constrained configuration by the delivery device, the implantable device defining a tube having an inner surface and an outer surface, in its constrained configuration; and releasing the implantable device from the delivery device into the blood vessel, thereby causing the implantable device to assume a non-constrained configuration by:

the inner surface at an upstream end of the implantable device inverting and radially expanding such as to contact an inner wall of the blood vessel, a central portion of the implantable device radially expanding such that, along the central portion of the implantable device, the inner surface defines diverging portion of a conduit, the conduit extending through the implantable device, and the diverging portion diverging in a direction from an upstream end of the conduit to a downstream end of the conduit, such that a cross-sectional area of the diverging portion of the conduit at its downstream end is greater than the cross-sectional area of the diverging portion of the conduit at its upstream end, and a downstream end of the implantable device radially expanding such that a downstream portion of the outer surface contacts an inner wall of the blood vessel.

In some applications, releasing the implantable device from the delivery device into the blood vessel includes releasing the implantable device from the delivery device into an aorta of the subject, and causing the implantable device to assume the non-constrained configuration includes causing the inner surface at the upstream end of the implantable device to invert at a location that is adjacent to aortic sinuses of the subject's aorta.

There is further provided, in accordance with some applications of the present invention, apparatus including:

an implantable device configured to be deployed in a blood vessel of a subject, the implantable device comprising:

an outer stent; and an inner structure configured to be coupled to the outer stent such that the outer stent is disposed outside at least a portion of the inner structure, the inner structure defining an inner surface that:

when the implantable device is in a deployed state within the blood vessel, is configured to define a conduit through the implantable device from a proximal end of the implantable device to a distal end of the implantable device, at least a portion of the conduit diverging in a direction from a proximal end of the conduit to a distal end of the conduit, such that a cross-sectional area of the conduit at its distal end is greater than the cross-sectional area of the conduit at its proximal end, and is configured to appose a wall of the blood vessel at a distal end of the inner surface; and the outer stent being configured to anchor the inner structure within the blood vessel by exerting a radial force upon a wall of the blood vessel, relative lengths of the outer stent and the inner structure being such that, when the inner structure is coupled to the outer stent, the inner structure extends beyond a distal end of the outer stent.

The present invention will be more fully understood from the following detailed description of embodiments thereof, taken together with the drawings, in which:

DETAILED DESCRIPTION OF EMBODIMENTS

Figure 1A:
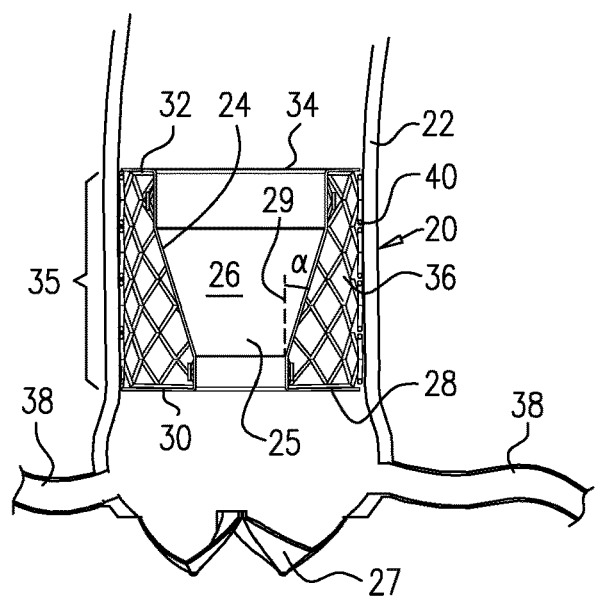
FIGS. 1A, 1B, 1C, and 1D are schematic illustrations of an implantable device deployed inside a subject's aorta, in accordance with some applications of the present invention.
Figure 1B:
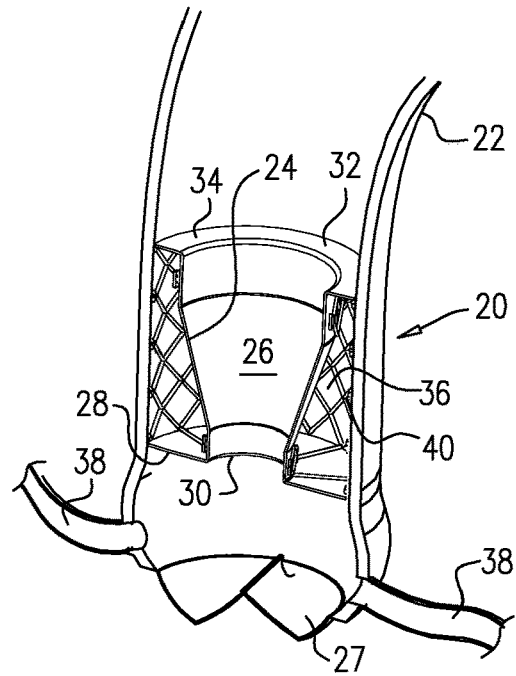
Figure 1C:
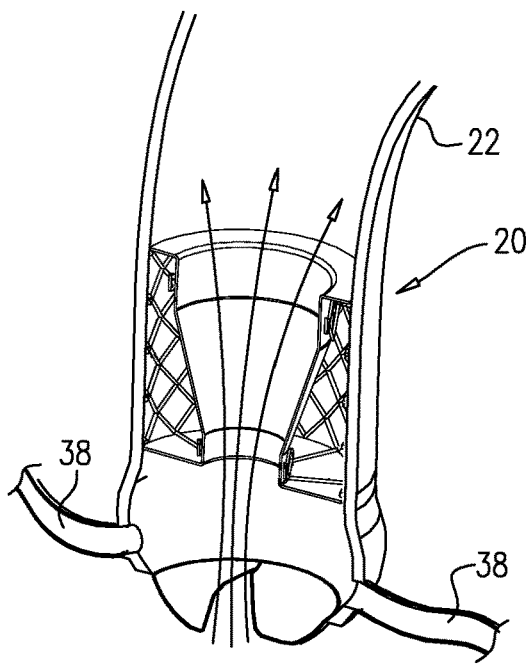
Figure 1D:
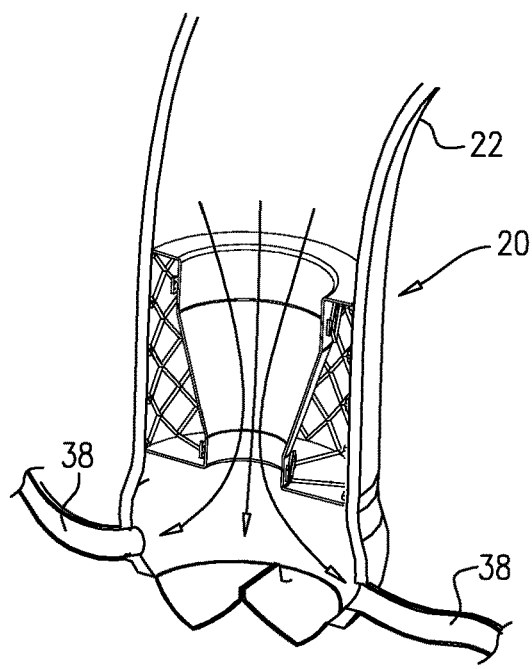

Reference is now made to FIGS. 1A-D, which are schematic illustrations of an implantable device 20 deployed inside a blood vessel of a subject (typically the subject's aorta 22 (e.g., ascending aorta), as shown), in accordance with some applications of the present invention. FIGS. 1C and 1D shows arrows representing blood flow during systole and diastole, respectively. As shown, device 20 defines an inner surface 24 that defines a conduit 26 through the device, from the proximal end of the device to the distal end of the device. At least a portion 25 of the conduit diverges in a direction from a proximal end of the conduit to a distal end of the conduit, such that the cross-sectional area of the conduit at the downstream end is greater than the cross-sectional area of the conduit at the upstream end. The device is typically placed in the ascending aorta of a subject suffering from aortic valve stenosis, in the vicinity of the stenosed aortic valve 27 (e.g., such that the upstream end of the conduit is downstream of the aortic valve, and within 25 mm from the aortic valve tip when the valve is in an open configuration, during systole). The blood exiting the subject's left ventricle, during systole, is directed into the conduit (FIG. 1C). The divergence of the conduit is configured to reduce pressure loss of blood flowing through the conduit, relative to the loss of pressure of the blood flowing through the longitudinal portion of the blood vessel in the absence of the device. The conduit reduces the blood pressure loss by reducing the area of flow separation. During diastole, blood flows back toward coronary arteries 38 via conduit 26 (FIG. 1D).

The device is typically deployed within a longitudinal portion of the aorta, such that blood flow through the longitudinal portion of the aorta, via any flow path other than through the conduit, whether in the antegrade or retrograde direction, is less than 20 percent (e.g., less than 10 percent, or less than 5 percent) of the total blood flow through the longitudinal portion of the blood vessel.

Typically, by directing the blood to flow in the above-described manner, loss of pressure and energy of the blood flow exiting the left ventricle into the ascending aorta is reduced relative to the loss of pressure and energy of the blood flow in the absence of the device. Thus, placement of device 20 in the subject's ascending aorta may decrease the subject's left ventricular pressure, reduce afterload, and/or and improve the subject's cardiac output. For some applications, regulating the blood flow from the aortic valve in the above-described manner may postpone or stop the degradation process leading to further aortic valve stenosis. An unhealthy flow regime in the ascending aorta can cause sequential deposits of thrombi on the valve surface that can cause further valve thickening, deformation and calcification leading to severe stenosis. Device 20, by changing the flow regime, may reduce the inflammatory process that causes the calcification. Thus, device 20 may decrease the degradation of the medical situation of the subject.

It is noted that, typically, device 20 does not include a prosthetic valve disposed within the conduit or at any other location within the device. The device typically performs all of the functions described herein without requiring the use of a prosthetic valve of any type.

Typically, the device includes a region disposed at the downstream end of the device that includes an outer circumference that is configured to appose a wall of the vessel in which the device is placed (e.g., the aorta). The device typically defines one or more surfaces (28, 32) that extend from the outside of the conduit to the inner wall of the blood vessel, and/or to an outer support structure 40 that is in contact with the inner wall of the blood vessel. Typically, the one or more surfaces extend radially outward, around the full circumference of the conduit, from the conduit at least to the radial location of the inner surface of the outer support structure (such that the surface extends to the inner surface of the blood vessel, and/or to the outer support structure). The surfaces are configured to impede the backflow of blood, around the outside of the conduit 26 (e.g., around the distal end of conduit 26), toward the aortic valve. For some applications, the device prevents any backflow of blood, around the outside of the conduit, toward the aortic valve.

Device 20 typically defines a proximal outer surface 28 that surrounds a proximal portion of conduit 26, and that extends at least from outside the conduit to outer support structure 40. For example, as shown in FIG. 1A-D, the proximal outer surface may be a disc-shaped surface that surrounds the proximal end 30 of conduit 26. Typically, the proximal outer surface is disposed around the conduit at a longitudinal location such that at least a portion of the proximal surface is within the proximal-most 30 percent (e.g., the proximal-most 20 percent) of the length of the conduit.

For some applications, device 20 defines a distal outer surface 32 that surrounds a distal portion of conduit 26, and that extends from outside the conduit to outer support structure 40. For example, as shown in FIG. 1A-D, the distal outer surface may be a disc-shaped surface that surrounds distal end 34 of the conduit. For some applications, the device does not define a separate distal outer surface. Rather, the distal end of the inner surface that defines the conduit extends to the inner wall of the blood vessel or to the outer support structure, which is in contact with the inner wall of the blood vessel. In this manner, the distal end of the inner surface acts as the distal outer surface, and impedes the backflow of blood around the outside of the distal end of the conduit, as shown in FIGS. 4B-E.

The proximal and distal outer surfaces are typically configured such that, when device 20 is deployed inside a longitudinal portion 35 of the subject's aorta, the surfaces substantially impede blood flow through longitudinal portion 35, via any flow path other than through conduit 26. For example, the proximal and distal surfaces may be configured such that, when the device is deployed inside the longitudinal portion of the subject's aorta, flow via flow paths other than through the conduit defined by the inner surface of the device, whether in the antegrade or retrograde direction, is less than 20 percent (e.g., less than 10 percent, or less than 5 percent) of total blood flow through the longitudinal portion of the subject's aorta. Typically, the proximal and distal surfaces are configured such that, when the device is deployed inside the longitudinal portion of the subject's aorta, there is no blood flow through the longitudinal portion of the subject's aorta via any flow path other than through the conduit defined by the inner surface of the device, whether in the antegrade or retrograde direction.

For some applications, (a) distal outer surface 32 is configured to impede the backflow of blood around the outside of conduit 26, and (b) proximal outer surface 28 is configured to impede antegrade blood flow around the outside of conduit 26. For example, proximal outer surface 28 may be configured to impede antegrade blood flow around the outside of the conduit, in order to reduce a likelihood of eddy currents and/or stagnated blood forming in the region surrounding the conduit. For some applications, the device includes a distal outer surface (or, the distal end of the inner surface that defines the conduit extends to the inner wall of the blood vessel or to the outer support structure, such that the distal end of the inner surface acts as the distal outer surface), and the device does not include a proximal outer surface (e.g., as shown in FIGS. 10A-B of WO 16/128983 to Karavany, which is incorporated herein by reference).

For some applications, the proximal outer surface, the distal outer surface, and/or the inner surface is impermeable and prevents blood from flowing back toward the aortic valve during systole (and/or during diastole), outside of the conduit. For some applications, by virtue of having both proximal and distal outer surfaces (or a proximal outer surface and an inner surface that extends to the inner wall of the blood vessel), the device is configured to trap any blood that is disposed within a region 36 between the conduit and the inner wall of the aorta within the longitudinal portion of the aorta in which the device is placed. In this manner, the device is configured to prevent any thrombi that develop within region 36 from exiting the region and entering the subject's bloodstream.

As described hereinabove, for some applications, the proximal outer, the distal outer, and/or the inner surfaces are not impermeable, but have a permeability that is sufficiently low as to substantially prevent any blood from flowing through the longitudinal portion of the aorta, via any flow path other than through the conduit defined by the inner surface of the device, in the manner described hereinabove.

For some applications, each of the surfaces has permeability per unit length of less than 0.25 micrometers (i.e., between 0 and 0.25 micrometers), where the permeability per unit length is defined based upon the following equation, which is based upon Darcy's Law:

$$k/\Delta x = V\mu/\Delta p$$

where k is permeability, $\Delta x$ is length (in meters), V is average velocity (in meters per second), $\mu$ is fluid viscosity (measured in Pascal-seconds), and $\Delta P$ is the pressure differential measured in Pascals).

For some applications, the proximal outer surface, the distal outer surface and/or the inner surface includes a material (such as a fabric, a metal, or an alloy) that is structured such that there are open spaces between portions of the material. For example, the material may be arranged in a lattice structure, a braided structure, a crisscross structure, a woven structure, a cellular structure, a stitched structure, or a similar structure. Typically, even for such applications, more than 20 percent of the area of each of the surfaces is filled with material, and less than 80 percent of the area of each of the surfaces is open space between the material. Further typically, more than 50 percent, e.g., more than 80 percent, of the area of each of the surfaces is filled with material. For some applications, there are no open spaces within the surfaces (i.e., the entirety of each of the surfaces is filled with material).

For some applications, the device is configured to promote coagulation of blood that is disposed within a region between the conduit and the inner wall of the aorta within the longitudinal portion of the aorta in which the device is placed, by substantially reducing blood flow through this region relative to in the absence of the device. Typically, the material that defines the proximal outer surface, the distal outer surface and/or the inner surface is configured to prevent any thrombi that develop within the region from exiting the region and entering the subject's bloodstream. For some applications, by promoting the coagulation of blood within the region, the device causes blood entering the region to become coagulated, such that the region becomes filled with coagulated blood within a given time period of the device being placed within the aorta (e.g., within one week, one month, or three months of the device being placed within the aorta), such that the coagulated blood impedes (e.g., blocks) the flow of blood through the region.

For some application, the blood that becomes coagulated within the region is blood that became trapped within the region immediately upon deployment of the device. Alternatively or additionally, blood enters the region subsequent to the device having been deployed, and the blood that subsequently enters the region becomes coagulated. It is noted that, even for such applications, the proximal and distal surfaces are configured such that, even when the device is first deployed and before coagulated blood has formed inside the region, flow via flow paths other than through the conduit defined by the inner surface of the device is less than 20 percent (e.g., less than 10 percent, or less than 5 percent) of total blood flow through the longitudinal portion of the subject's aorta. For some applications, techniques are applied in order to coagulate blood that is trapped within region 36. For example, coil compaction techniques may be applied in order to cause the blood to coagulate.

Typically, when device 20 is deployed inside the subject's ascending aorta, blood is supplied to the subject's coronary arteries 38 via backflow of blood through conduit 26 during diastole (FIG. 1D), and/or via blood flowing directly from the aortic valve to the coronary arteries without passing into conduit 26 (not shown). For some applications, a portion of the blood supply to the coronary arteries is provided by antegrade blood flow from the aortic valve to the coronary arteries (e.g., during systole). Typically, most of the blood supply to the coronary arteries is via the backflow of blood through conduit 26 during diastole.

As stated above, at least portion 25 of conduit 26 diverges in a direction from proximal end 30 of the conduit to distal end 34 of the conduit. Due to the divergence of the portion of the conduit, the cross-sectional area of the proximal end of the diverging portion of the conduit is greater than the cross-sectional area of the distal end of the conduit. For some application, the divergence of the conduit along the diverging portion of the conduit is at a constant angle alpha (FIG. 1A) along the length of the diverging portion of the conduit, for example, such that the diverging portion of the conduit defines a frustoconical shape, as shown. For some applications, the angle of the divergence of the conduit along the diverging portion of the conduit changes along the length of the diverging portion of the conduit. For example, the angle of the divergence may increase from the proximal end of the portion to the distal end of the portion, such that inner surface 24 has a convex cross-section along the diverging portion of the conduit. For some applications, the diverging portion of the conduit defines a stratford ramp shape. Typically, the proximal and distal ends of the diverging portion of the conduit define circular cross-sections. Alternatively, the proximal and distal ends of the diverging portion of the conduit define elliptical cross-sections, polygonal cross-sections, or differently shaped cross-sections.

Typically, the angle of divergence alpha (which is measured with respect to a line 29 that is parallel to the longitudinal axis of the conduit, as shown in FIG. 1A), or the average angle of divergence, in cases in which the divergence varies along the length of the conduit, is greater than 1 degree (e.g., greater than 5 degrees, and less than 30 degrees (e.g., less than 20 degrees), e.g., 1-30 degrees, or 5-20 degrees). For some applications, angle alpha is less than 5 degrees, e.g., 1-5 degrees. For some applications (not shown), device 20 is generally as described herein, except that rather than portion 25 diverging, portion 25 is shaped cylindrically, i.e., angle alpha is 0. For some applications (not shown), rather than the diameter of the diverging portion increasing in a gradual manner, the diameter of the diverging portion increases in a stepwise manner.

Figure 2A:
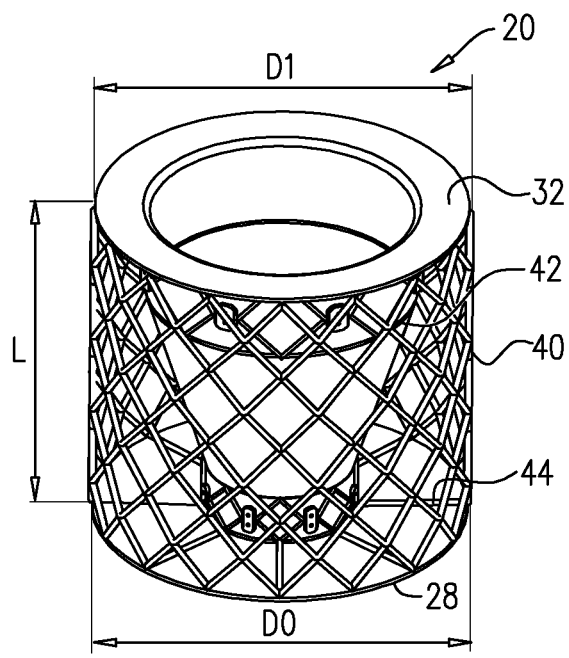
FIGS. 2A, 2B, and 2C are schematic illustrations of a device for implanting inside a blood vessel of a subject, in accordance with some applications of the present invention.
Figure 2B:
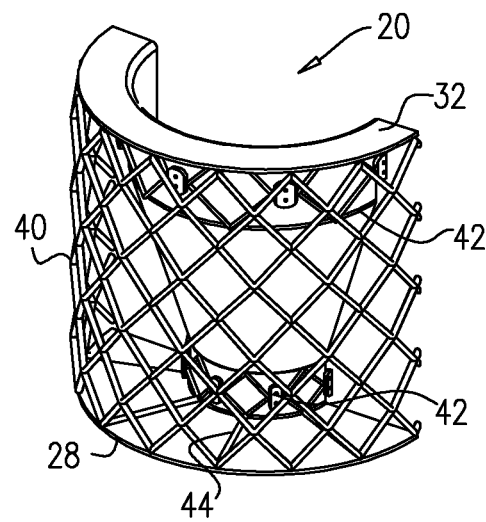
Figure 2C:
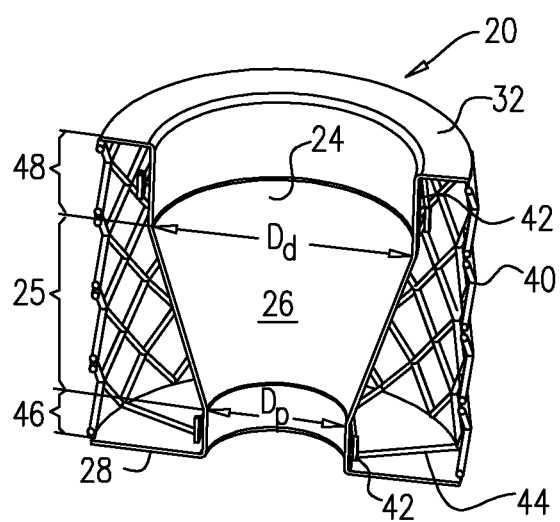

Reference is now made to FIGS. 2A-C, which are schematic illustrations of respective views of implantable device 20, in accordance with some applications of the present invention. As shown, for some applications, device 20 includes outer support structure 40. The outer support structure maintains device 20 within the blood vessel (e.g., the aorta) by contacting the inner wall of the blood vessel. For some applications, the outer support structure is a stent-like structure, the outer support structure being shaped as a cylindrical stent, and/or the support structure including struts of a metal or alloy, such as stainless steel or nitinol. When device 20 is deployed inside the subject's ascending aorta, the outer support structure anchors the device within the ascending aorta, by expanding such as to exert an outward radial force upon the inner wall of the aorta. Typically, the outer support structure at least partially overlaps with the conduit, along the axial direction of the device, and the outer support structure is disposed around the outside of at least a portion of the conduit. For some applications, the outer support structure is configured such that an interface between the outer support structure and the inner wall of the blood vessel is sealed. For example, the outer support structure may be at least partially covered with a cover that seals the interface between the outer support structure and the inner wall of the blood vessel. For some applications, a different portion of the device is configured to form a seal between the device and the inner wall of the blood vessel, such that there is substantially no blood flow between the device and the inner wall of the blood vessel.

Typically, inner surface 24 is made of a flexible material that has low permeability (e.g., as described herein), such as expanded polytetrafluoroethylene (ePTFE) or woven polyester. The inner surface is supported by an inner support structure 42, which typically comprises struts of a metal or alloy, such as stainless steel or nitinol. For some applications, inner support structure and outer support structure are coupled to each other via rigid coupling elements 44, such as struts, as shown. Typically, coupling elements 44 also support proximal outer surface 28 and distal outer surface 32. For some applications, the proximal and distal outer surfaces are made of a similar material to that of inner surface 24. For some applications, inner surface 24, proximal outer surface 28, and/or distal outer surface 32 are made of a single continuous piece of material. Alternatively or additionally, inner surface 24, proximal outer surface 28, and/or distal outer surface 32 are formed separately from one another and are coupled to one another such that any interfaces between the surfaces are substantially sealed.

In general, device 20 as described with respect to any of the applications of the present invention may include any combination of modularly-formed components (i.e., components that are formed separately from one another) which are subsequently coupled to one another. Typically, the modularly-formed components are coupled to one another such that any interfaces between the components are substantially sealed.

Typically, proximal outer surface 28 extends radially outward from the edge of the layer of material that defines inner surface 24 to the inner surface of outer support structure 40. Similarly, for applications in which device 20 includes distal outer surface 32, the distal outer surface extends radially outward from the edge of the layer of material that defines inner surface 24 to the inner surface of the outer support structure. For some applications, the distal end of the inner surface extends radially outward to the inner wall of the blood vessel, and/or to the inner surface of the outer support structure, which is contact with the inner wall of the blood vessel, e.g., in the manner described with reference to FIGS. 4A-E, such that the distal end of the inner surface impedes blood flow around the outside of the distal end of the conduit.

For some applications, inner surface 24 that defines conduit 26 is rough. The rough surface of the conduit is configured to act as a turbulator on the boundary layer between the blood and the surface of the conduit, such as to increase adhesion, excite the boundary layer, and delay flow separation.

Typically, device 20 is inserted into the subject's aorta (e.g., ascending aorta) via a catheter. In order to deploy the device inside the aorta, the catheter is retracted, in response to which the device is configured to self-expand. For some applications, during the self-expansion of the device, the device traps blood between the inner wall of the aorta, conduit 26, proximal outer surface 28, and distal outer surface 32. For some applications, techniques are applied in order to cause the trapped blood to coagulate. For example, coil compaction techniques may be applied in order to cause the blood to coagulate. For some applications, device 20 is a balloon-expandable device that is configured to be expanded inside the ascending aorta by a balloon being inflated inside the device.

With reference to FIG. 2A, it is noted that, typically, length L of device 20 is greater than 20 mm (e.g., greater than 30 mm), and/or less than 70 mm (e.g., less than 60 mm), e.g., 20-70 mm, or 30-60 mm. For some applications, the length of diverging portion 25 of conduit 26 (measured along the longitudinal axis of the device) is greater than 20 mm (e.g., greater than 30 mm), and/or less than 70 mm (e.g., less than 60 mm), e.g., 20-70 mm, or 30-60 mm, and length L of the device is greater than the length of diverging portion 25. For some applications, a ratio of (a) an outer diameter D0 of a proximal end of outer support structure 40 to (b) an outer diameter D1 of the distal end of the outer support structure is greater than 3:4, and/or less than 4:3, e.g., between 3:4 and 4:3. Outer diameter D0 of the proximal end of the outer support structure is typically made to conform with the inner diameter of the subject's aorta toward the proximal end of the device, and outer diameter D1 of the distal end of the outer support structure is typically made to conform with the inner diameter of the subject's aorta at the distal end of the device. Since there is some variation in the shapes and sizes of subject's aortas, the ratio of D0:D1 typically varies between 3:4 and 4:3. Typically, the maximum outer diameter of the device (i.e., the outer diameter of the device at the location along the length of the device at which the outer diameter is at its maximum) is greater than 18 mm (e.g., greater than 25 mm), and/or less than 45 mm (e.g., less than 35 mm), e.g., 18-45 mm, or 25-35 mm.

Further typically, with reference to FIG. 2C, it is noted that the difference between a proximal inner diameter Dp of conduit 26 at the proximal end of diverging portion 25 of the conduit, and a distal inner diameter Dd of conduit 26 at the distal end of the diverging portion of the conduit is greater than 3 mm (e.g., greater than 5 mm, or greater than 10 mm), and/or less than 30 mm (e.g., less than 20 mm), e.g., 5-30 mm, or 10-20 mm. Typically, proximal inner diameter Dp is greater than 7 mm, and/or less than 14 mm, e.g., 7-14 mm. Further typically, distal inner diameter is greater than 12 mm and/or less than 44 mm, e.g. 12-44 mm.

For some applications, the ratio of diameter Dd of conduit 26 at the distal end of diverging portion 25 of the conduit to diameter Dp of the conduit at the proximal end of the diverging portion of the conduit is greater than 4:3 (e.g., greater than 2:1), and/or less than 4:1 (e.g., less than 3:1), e.g., 4:3-4:1, or 2:1-3:1. It is noted that the cross-section of the conduit is not necessarily circular. For applications in which the term "diameter" is used with reference to an object or a portion of an object having a non-circular cross-section, the term "diameter" should be interpreted as meaning the hydraulic diameter, i.e. 4A/P (where A is the cross-sectional area, and P is the perimeter).

For some applications, the ratio of diameter Dd of conduit 26 at the distal end of diverging portion 25 of the conduit to diameter Dp of the conduit at the proximal end of the diverging portion of the conduit is less than 4:3, for example between 5:4 and 7:6 (e.g., 6:5). For some such applications, the difference between diameter Dd and diameter Dp is less than 3 mm, or less than 2 mm. By way of example, Dd may be 14.5 mm and Dp may be 13 mm. It is noted that, even with devices with diameters Dd and Dp as described in the present paragraph, the inventors of the present application have found that some of the beneficial results of placing the device in the aorta of a subject with aortic valve stenosis are likely to be achieved, based upon in vitro experiments that were performed with such devices using a model of the aortic valve and the ascending aorta with a pulse generator. Moreover, the inventors of the present application have found that some of the beneficial results of placing the device in the aorta of a subject with aortic valve stenosis are likely to be achieved even with a device in which portion 25 of the conduit does not diverge, but is cylindrical, based upon in vitro experiments that were performed with such devices using a model of the aortic valve and the ascending aorta with a pulse generator. Therefore, the scope of the present invention includes a device that is generally like device 20 described herein, but in which portion 25 of conduit 26 does not diverge, but is cylindrical, and methods of use of such a device, mutatis mutandis. For some applications (not shown), rather than the diameter of the diverging portion increasing in a gradual manner, the diameter of the diverging portion increases in a stepwise manner.

It is noted that, typically, the dimensions of device 20 described herein are the dimensions that the device is configured to have, when the device is in a non-constrained state. Typically, if the device is inserted via an insertion catheter, the device is constrained during its insertion, such that the dimensions of the device during the insertion may not be as described herein. However, when the device is in a deployed state inside a blood vessel of the subject (e.g., inside the subject's aorta), the device is typically configured to have dimensions as described herein, since, when deployed inside the blood vessel, the device assumes its "non-constrained" configuration. It is further noted that, for some applications the device is implanted in a non-minimally-invasive manner (e.g., using traditional surgical techniques). For some such applications, even during the insertion of the device, the device is configured in its non-constrained state.

With reference to FIG. 2C, it is noted that, for some applications, conduit 26 defines a proximal portion 46 that is disposed proximally to diverging portion 25, and/or a distal portion 48 that is distal to diverging portion 25. For some applications, as shown, proximal portion and/or distal portion have cylindrical shapes. Alternatively or additionally, proximal portion and/or distal portion may have a different shape. For example, one or both of the portions may have an elliptical cross-section along a plane that is perpendicular to the longitudinal axis of the conduit. For some applications, the proximal portion converges in the proximal to distal direction in order to direct blood from the aortic valve to diverging portion 25 of the conduit, e.g., as shown in FIGS. 4B, and 6B, for example. For some applications, the distal portion is shaped such that when device 20 is disposed inside the ascending aorta, the distal portion curves toward the aortic arch, such that blood is directed toward the aortic arch, e.g., as described in further detail hereinbelow with reference to FIGS. 5A-5D.

As shown in FIG. 2C, for some applications, the proximal end of conduit 26 is level with the proximal end of outer support structure 40, such that surface 28, which surrounds the proximal end of the conduit and extends to the proximal end of the outer support structure, defines a flat disc shape. However, for some applications (not shown), the proximal end of the conduit extends in the proximal direction beyond the proximal end of the outer support structure. Alternatively, the proximal end of the outer support structure extends in the proximal direction beyond the proximal end of the conduit. For such applications, surface 28 is typically disposed at an angle with respect to a plane that is perpendicular to the longitudinal axis of the conduit. For some applications, surface 28 is curved. For example, the surface may be concave or convex.

Similarly, as shown in FIG. 2C, for some applications, the distal end of conduit 26 is level with the distal end of outer support structure 40, such that surface 32, which surrounds the distal end of the conduit and extends to the distal end of the outer support structure, defines a flat disc shape. However, for some applications (not shown), the distal end of the conduit extends in the distal direction beyond the distal end of the outer support structure. Alternatively, the distal end of the outer support structure extends in the distal direction beyond the distal end of the conduit. For such applications, surface 32 is typically disposed at an angle with respect to a plane that is perpendicular to the longitudinal axis of the conduit. For some applications, surface 32 is curved. For example, the surface may be concave or convex. As noted hereinabove, for some applications, the device does not define a separate distal outer surface. Rather, the distal end of the inner surface that defines the conduit extends to the inner wall of the blood vessel, and/or to the outer support structure, which is in contact with the inner wall of the blood vessel, such that the distal end of the inner surface impedes the backflow of blood around the outside of the distal end of the conduit, as shown in FIGS. 4A-E.

Figure 3A:
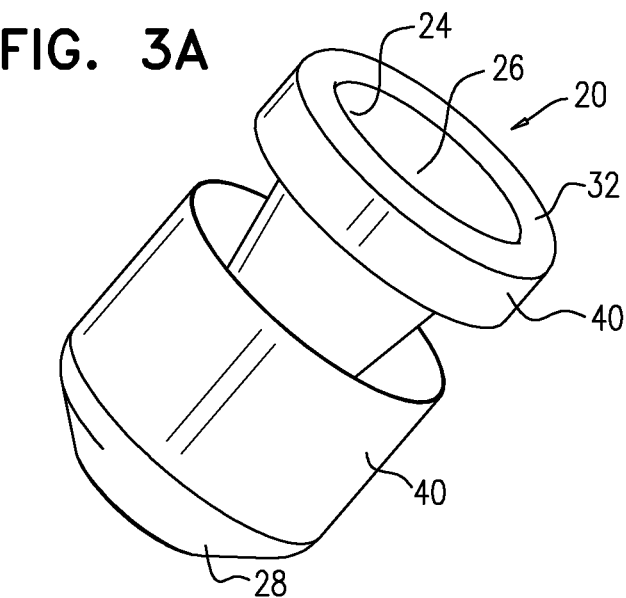
FIGS. 3A, 3B, and 3C are schematic illustrations of respective views of a device for implanting inside a blood vessel of a subject, in accordance with some applications of the present invention.
Figure 3B:
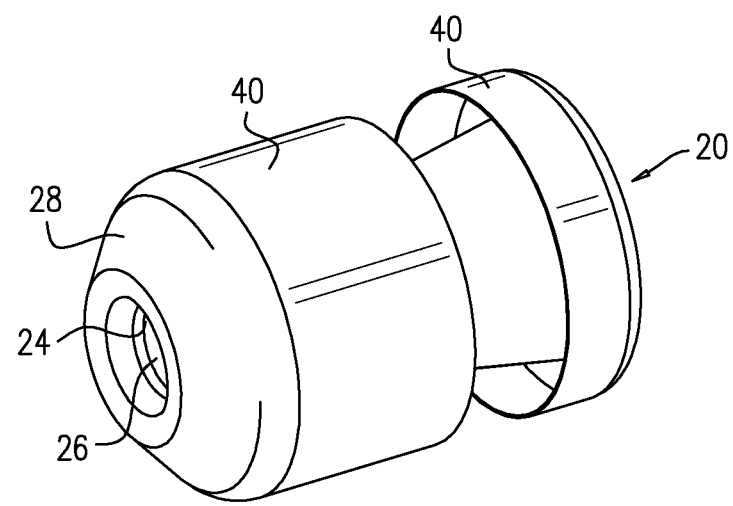
Figure 3C:
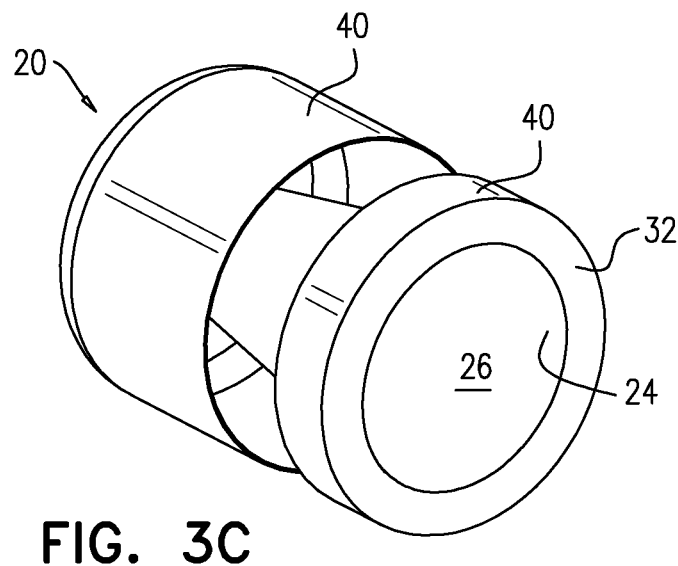

Reference is now made to FIGS. 3A-C, which are schematic illustrations of device 20, the device being made of stent graft material, in accordance with some applications of the present invention. FIGS. 3A-C show respective three-dimensional views of the device. Device 20 as shown in FIGS. 3A-C is generally similar to device 20 as described hereinabove, except for the differences described hereinbelow.

For some applications, inner surface 24, proximal outer surface 28, distal outer surface 32, and outer support structure 40 are all formed of a single continuous portion of graft material. The graft material is typically formed from a combination of a metal or alloy frame (e.g., a stent made of stainless steel or nitinol) and fabric (such as expanded polytetrafluoroethylene (ePTFE) or woven polyester). For some applications, the frame of the stent graft material is a braided stent. For some applications, the braided stent provides flexibility to the device that facilitates insertion of the device via curved portions of the vasculature. For some applications, using a braided stent allows the device to be radially constrained to a narrower diameter than would be possible using a non-braided stent.

As described hereinabove, typically, outer support structure 40 at least partially overlaps with the conduit, along the axial direction of the device, and the outer support structure is disposed around the outside of at least a portion of the conduit. FIGS. 3A-C show the device with outer support structure 40 not being continuous along the length of the device, but including support rings that are disposed distally to the proximal outer surface and proximally to the distal outer surface, in accordance with some applications of the present invention. However, the scope of the present invention includes using a continuous portion of graft material to form a device having any one of the other structures described herein. For example, the graft material could be used to form a device that does not define a distal outer surface, but which defines an inner surface that extends to the inner wall of the blood vessel (as shown in FIGS. 4A-E). Or, the graft material could be used to form a device having an outer support structure that runs continuously along the length of the device (e.g., as shown in FIGS. 1A-D). For some applications, graft material is used to form device 20, but the device is not formed from a single portion of graft material. Rather, the device may be formed from a plurality of pieces of graft material that are coupled to each other.

Figure 4A:
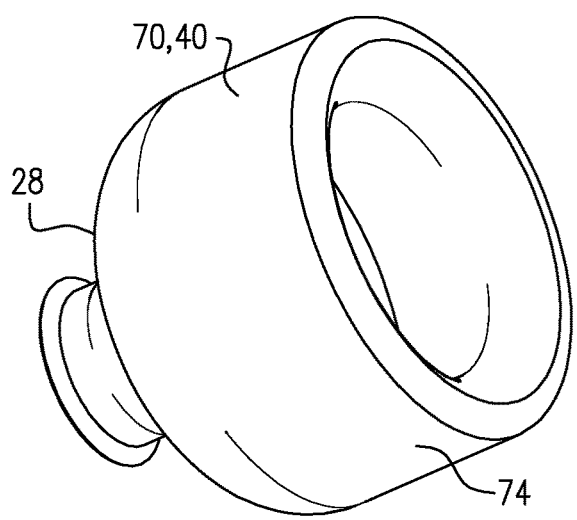
FIGS. 4A, 4B, 4C, 4D, and 4E are schematic illustrations of a device for implanting inside a blood vessel of a subject, and components of the device, in accordance with some applications of the present invention.
Figure 4B:
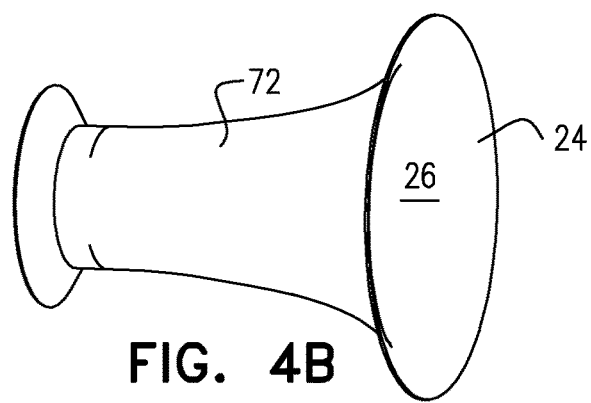
Figure 4C:
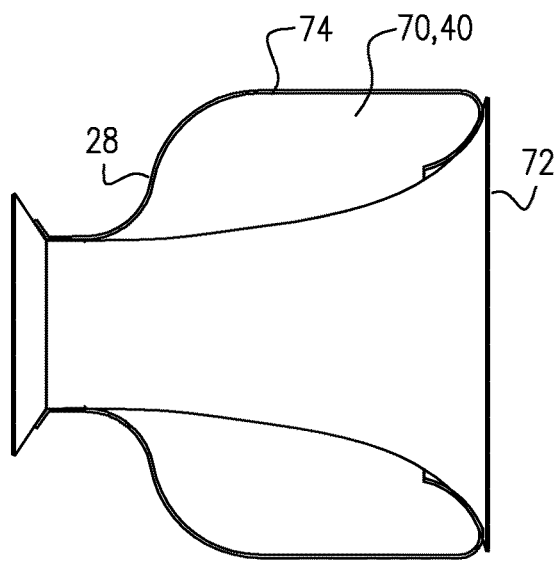
Figure 4D:
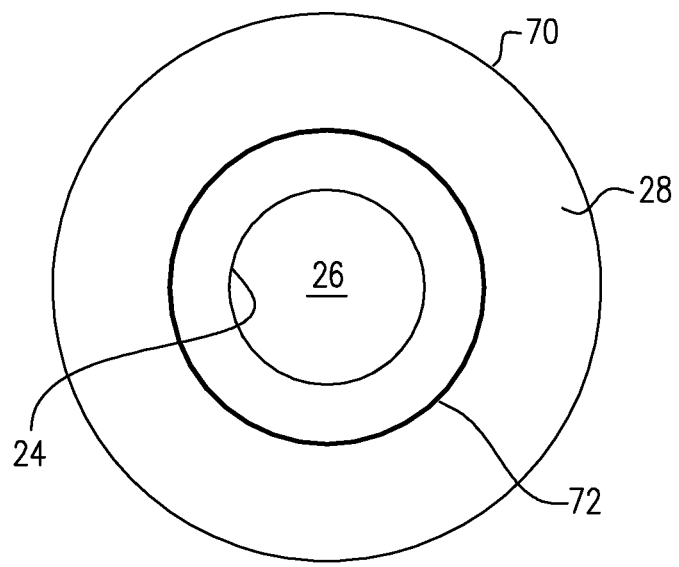
Figure 4E:
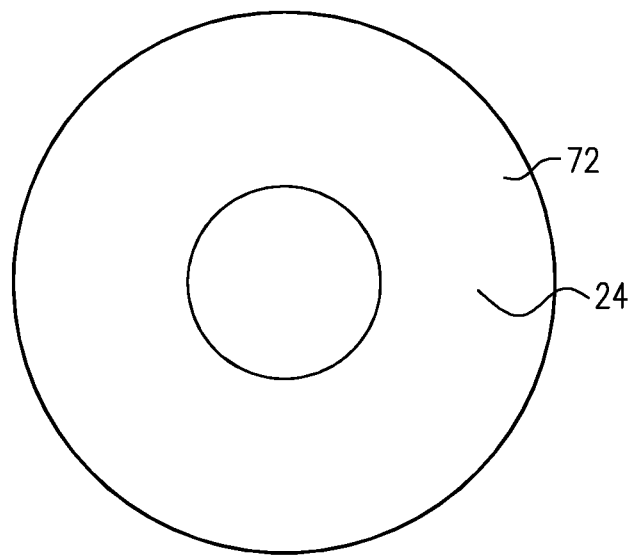

Reference is now made to FIGS. 4A-E, which are schematic illustrations of components of device 20, for implanting inside a blood vessel of a subject (e.g., the subject's ascending aorta, as described hereinabove), in accordance with some applications of the present invention. For some applications, device 20 includes an outer stent 70 and an inner structure 72 that defines conduit 26. FIG. 4A shows outer stent 70, FIG. 4B shows inner structure 72, and FIGS. 4C-E show respective views of the inner structure disposed inside the outer stent, in the manner in which the inner structure and outer stent are typically deployed inside the subject's blood vessel (e.g., inside the subject's ascending aorta).

Outer stent is configured to anchor device 20 within the aorta, by outer surface 74 of the stent exerting a radial force upon the inner wall of the aorta. In this regard, the outer stent functions as outer support structure 40, as described hereinabove. In accordance with respective applications, the outer stent is self-expandable, or is balloon-expandable. Inner structure is configured to be disposed inside the outer stent and for the inner surface of the inner structure to define conduit 26. In accordance with respective applications, the inner structure is self-expandable, or is balloon-expandable.

For some applications, the outer stent and the inner structure are inserted into the subject's aorta simultaneously, with the inner structure already disposed inside the outer stent. For some applications, the outer stent and the inner structure are a single integrated structure, or are coupled to one another. Typically, for such applications, the outer stent and the inner structure are deployed in a single deployment step. For example, the outer stent and the inner structure may be allowed to self-expand, or be expanded using a balloon, at the time as one another. Alternatively, the outer stent and the inner structure are inserted and/or deployed in separate insertion and/or deployment steps. For example, the outer stent may first be deployed (e.g., via self-expansion or via balloon expansion) inside the aorta, such that the outer stent becomes anchored in position within the aorta. Subsequently, the inner stent may be deployed (e.g., via self-expansion or via balloon expansion) inside the outer stent.

FIGS. 4C-E show respective views of the inner structure disposed inside the outer stent. FIG. 4C shows a lateral transparent view of the outer stent and the inner structure, and FIGS. 4D and 4E show, respectively, proximal and distal end views of the outer stent and the inner structure.

As may be observed in FIGS. 4C-4D, outer stent 70 defines proximal surface 28, which extends from outside conduit 26 to the portion of the outer stent that is contact with the inner wall of the blood vessel. The proximal surface is configured to substantially prevent antegrade blood flow around the outside of the conduit, for example, in order to reduce a likelihood of eddy flow and/or stagnated blood forming in the region surrounding the conduit. Typically, the proximal outer surface is disposed around conduit 26 such that at least a portion of the surface is at a longitudinal location that is within the proximal-most 30 percent of the length of the conduit.

As may be observed in FIGS. 4C and 4E, in accordance with some applications of the present invention, device 20 does not define a separate distal outer surface. Rather, the distal end of the inner surface 24 that defines the conduit extends to the inner wall of the blood vessel, such that the circumference of the distal end of the inner surface apposes the inner wall of the blood vessel, and such that the distal end of the inner surface impedes the backflow of blood around the outside of the distal end of the conduit. Typically, the distal end of the inner surface impedes the backflow of blood around the outside of the distal end of the conduit in a generally similar manner to that described hereinabove with respect to the distal outer surface. For example, the inner surface may be impermeable, and/or may have a permeability per unit length of less than 0.25 micrometers (as described hereinabove). For some applications, the inner surface includes a material (such as a fabric, a metal, or an alloy) that is structured such that there are open spaces between portions of the material. For example, the material may be arranged in a lattice structure, a braided structure, a crisscross structure, a woven structure, a cellular structure, a stitched structure, or a similar structure. Typically, even for such applications, more than 20 percent of the area of the inner surface is filled with material, and less than 80 percent of the area of the inner surface is open space between the material. Further typically, more than 50 percent, e.g., more than 80 percent, of the area of each of the inner surface is filled with material. For some applications, there are no open spaces within the inner surface (i.e., the entirety of the inner surface is filled with material).

Figure 5A:
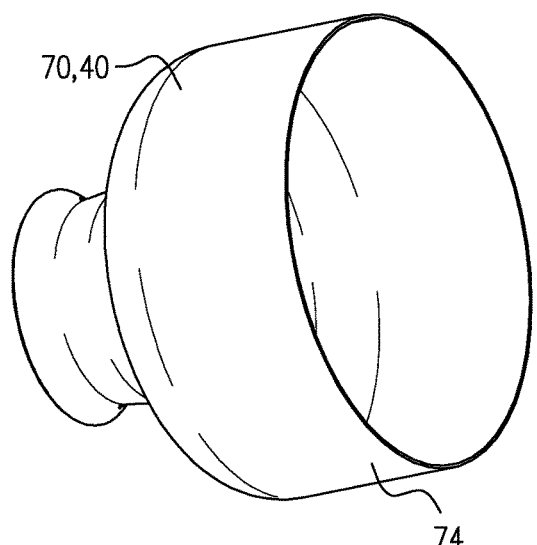
FIGS. 5A, 5B, 5C, and 5D are schematic illustrations of a device for implanting inside a blood vessel of a subject, and components of the device, in accordance with some applications of the present invention.
Figure 5B:
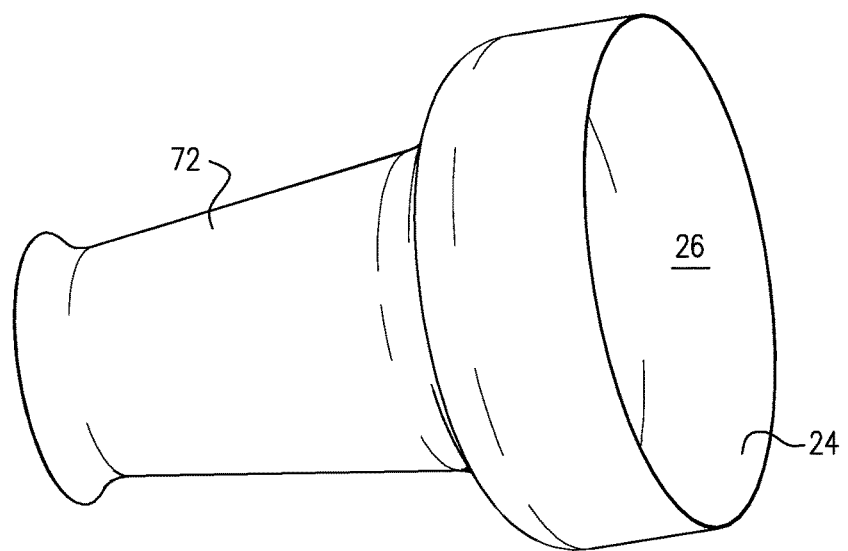
Figure 5C:
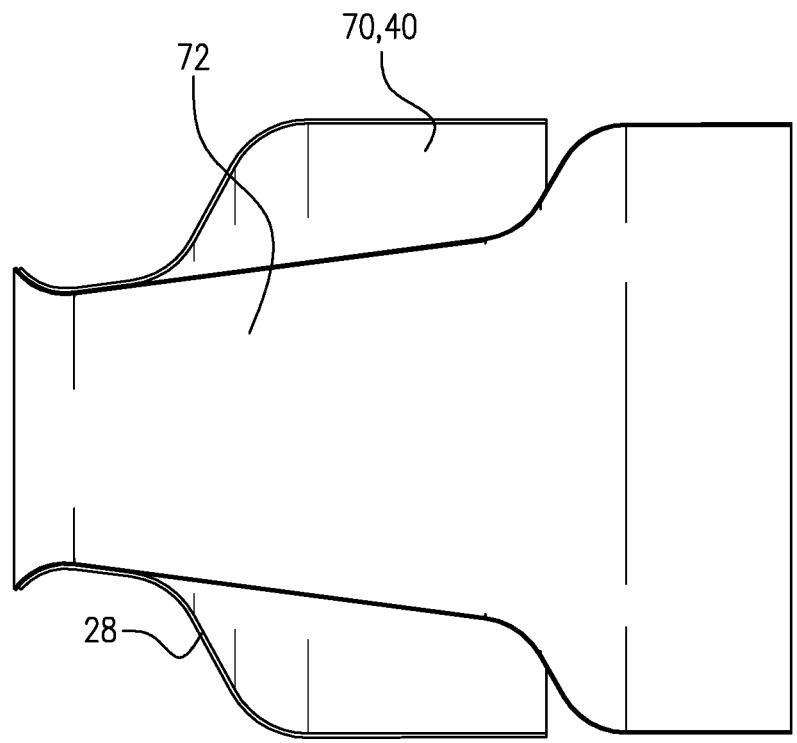
Figure 5D:
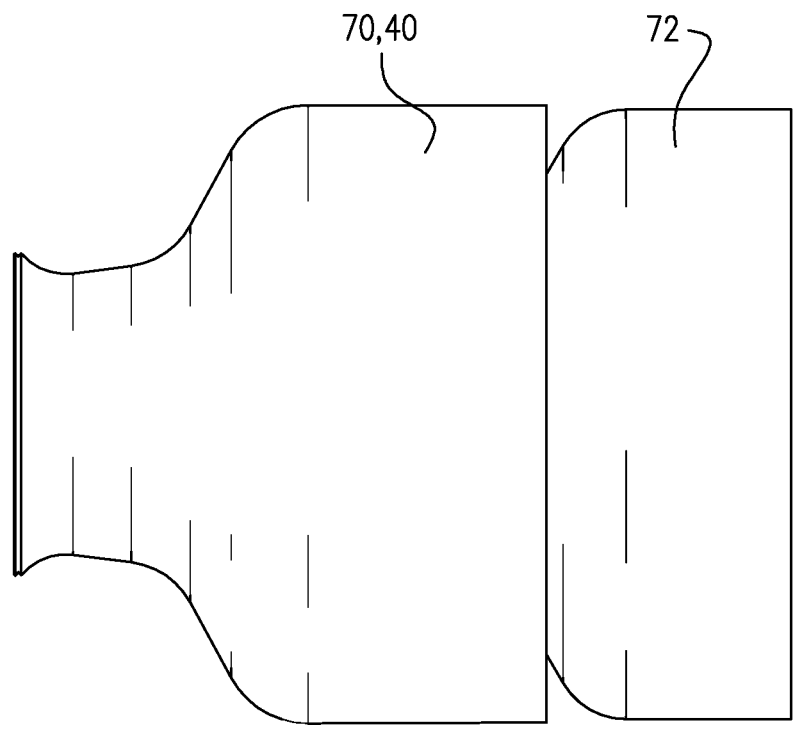

Reference is now made to FIGS. 5A-D, which are schematic illustrations of components of device 20, for implanting inside a blood vessel of a subject (e.g., the subject's aorta, as described hereinabove), in accordance with some applications of the present invention. As described with reference to FIGS. 4A-E, for some applications, device 20 includes an outer stent 70 and an inner structure 72 that defines conduit 26. FIG. 5A shows outer stent 70, FIG. 5B shows inner structure 72, and FIGS. 5C-D show, respectively, a cross-sectional view and a three-dimensional side view of the inner structure disposed inside the outer stent, in the manner in which the inner structure and outer stent are typically deployed inside the subject's blood vessel (e.g., inside the subject's aorta). Device 20 as shown in FIGS. 5A-D is generally similar to that shown and described with reference to FIGS. 4A-E, except that as shown in FIGS. 5A-D, the outer stent does not extend all the way to the distal end of the inner structure, in accordance with some applications of the present invention. Typically, relative lengths of the outer stent and the inner structure are such that, when the inner structure is coupled to the outer stent, the inner structure extends beyond a distal end of the outer stent. For some applications, the length of the outer stent is less than 80 percent, e.g., less than 60 percent, or less than 50 percent of the length of the inner structure.

Typically, outer stent 70 is configured to be placed downstream of the aortic valve (e.g., within 25 mm from the aortic valve tip, when the valve is in an open configuration during systole), and is configured to anchor device 20 in place within the subject's aorta, by outer surface 74 of the outer stent exerting a radial force on the inner wall of the aorta. In this regard, the outer stent functions as outer support structure 40, as described hereinabove. Inner structure 72 is typically coupled to the outer stent, and is longitudinally anchored in position within the aorta by the outer stent. For some applications, the inner structure is configured to be able to at least partially conform with the curvature of the aorta, such that, for example, the distal end of the inner structure may extend into the aortic arch, and conform at least partially with the curvature of the aortic arch. As described hereinabove, in accordance with respective applications, the outer stent and the inner structure are inserted into and/or deployed within the subject's aorta in a single deployment step, or the outer stent and the inner structure are inserted and/or deployed in separate insertion and/or deployment steps. For some applications, by the outer stent and the inner structure being inserted separately, the diameter to which device 20 can be constrained during transcatheteral insertion of the device is reduced relative to if the outer stent and the inner structure are inserted into the aorta together with each other.

For some applications, using a shortened outer stent (i.e., an outer stent that is shorter than the inner structure) as shown in FIGS. 5A-D facilitates delivery of the outer stent to the subject's aorta, e.g., by making it easier for the outer stent to navigate turns while being inserted transcatheterally. For some applications, the distal end of the device forms a better seal with respect to the subject's aorta using a configuration as shown in FIGS. 5A-D, relative to a device as shown in FIGS. 4A-E for example, because the inner structure and the outer stent separately form seals against the inner wall of the aorta at the distal ends of each of the components. Alternatively, for some applications, the distal end of the device forms a better seal with respect to the subject's aorta using a configuration as shown in FIGS. 4A-E, relative to a device as shown in FIGS. 5A-D for example, since using the device as shown in FIGS. 4A-E, both the distal end of the inner structure and the distal end of the outer stent exert radial forces upon the same longitudinal location along the wall of the aorta. For some applications, using a configuration as shown in FIGS. 5A-D reduces wear at the distal end of the device, relative to a device as shown in FIGS. 4A-E for example, because the distal ends of the inner structure and the outer stent do not rub against each other.

For some applications in which device 20 includes an outer stent 70 and an inner structure 72 (e.g., as shown in FIGS. 4A-E and FIGS. 5A-D), a sealing material (not shown) seals an interface between the outer stent and the inner structure. For example, the sealing material may include a skirt made of a polymer such as PET, or silicone that is disposed at the interface between the outer stent and the inner structure.

Figure 6A:
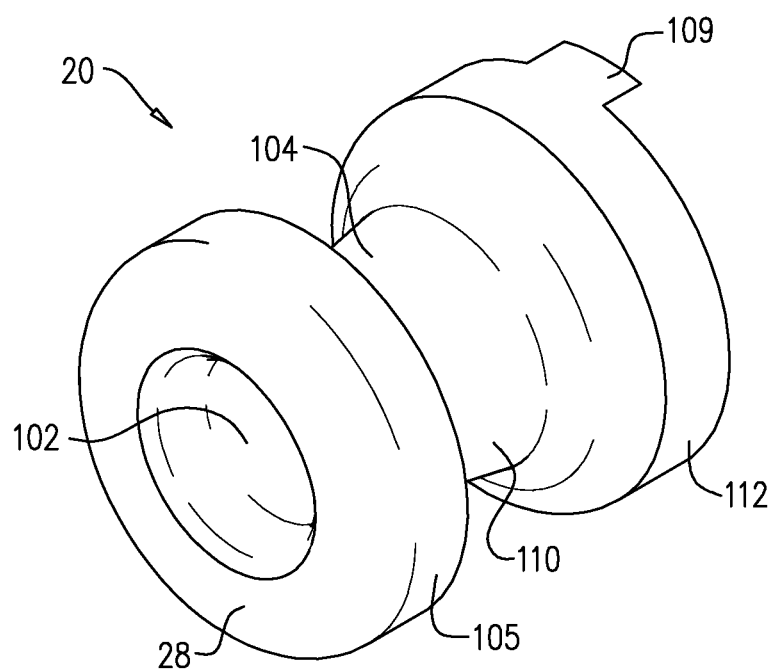
FIGS. 6A and 6B are schematic illustrations of a device for implanting inside a blood vessel of a subject, in accordance with some applications of the present invention.
Figure 6B:
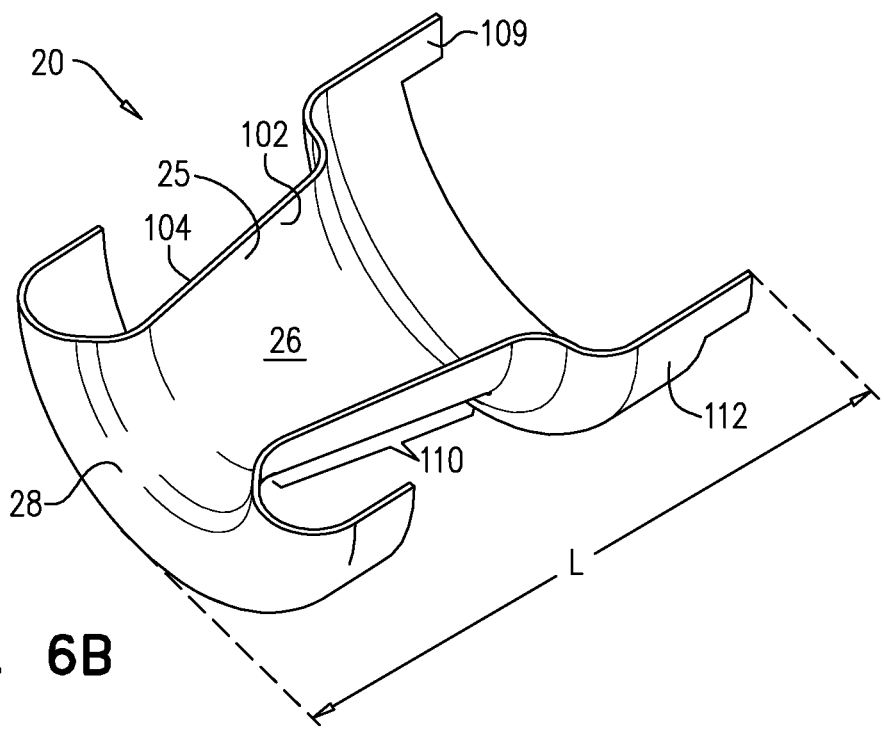

Reference is now made to FIGS. 6A and 6B, which are schematic illustrations of device 20 for implanting inside a blood vessel of a subject, in accordance with some applications of the present invention. FIG. 6A shows a three-dimensional view of the device, and FIG. 6B shows a cross-sectional view of the device, both FIGS. 6A and 6B showing the device in its non-constrained configuration. Device 20 as shown in FIGS. 6A and 6B is generally similar to device 20 as shown in FIGS. 3A-C, except for the differences described hereinbelow. As described with reference to FIG. 3A-C, for some applications, device 20 is formed from a single continuous portion of graft material. The graft material is typically formed from a combination of a metal or alloy frame (e.g., a stent made of stainless steel or nitinol) and fabric (such as expanded polytetrafluoroethylene (ePTFE) or woven polyester). For some applications, the frame of the stent graft material is a braided stent. For some applications, the braided stent provides flexibility to the device that facilitates insertion of the device via curved portions of the vasculature. For some applications, using a braided stent allows the device to be radially constrained to a narrower diameter than would be possible using a non-braided stent.

Figure 7A:
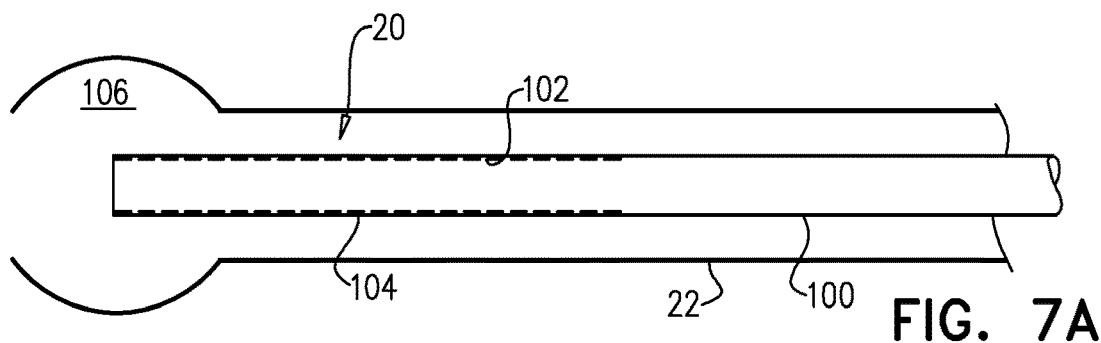
FIGS. 7A, 7B, 7C, and 7D are schematic illustrations of respective steps of the device of FIGS. 6A and 6B being implanted inside a subject's aorta, in accordance with some applications of the present invention.

Reference is also made to FIGS. 7A, 7B, 7C, and 7D, which are schematic illustrations of respective steps of the device 20 as shown in FIGS. 6A and 6B being implanted inside the subject's aorta 22, in accordance with some applications of the present invention. Typically, device 20 is inserted into the subject's aorta via a delivery device, such as a catheter 100 (as shown). For some applications, one or more protruding portions 109 protrude from the downstream end of device 20, and device 20 is held is the delivery device via the protruding portions. While device 20 is disposed inside the delivery device, the delivery device constrains device 20 in a constrained configuration, in which device 20 defines a tube, having an inner surface 102 and an outer surface 104 (as shown in FIG. 7A). It is noted that since device 20 is formed from graft material, typically the tube includes folds on its surfaces, due to folding of the graft material. Moreover, the device does not necessarily define a precise cylindrical tube in this configuration. Rather, the device typically has a generally tubular shape in which the device defines inner surface 102 and outer surface 104. In order to implant device 20 inside the subject's aorta, device 20 is released from the delivery device, e.g., by retracting the delivery device. Releasing device 20 from the delivery device causes device 20 to assume its non-constrained configuration.

Figure 7B:
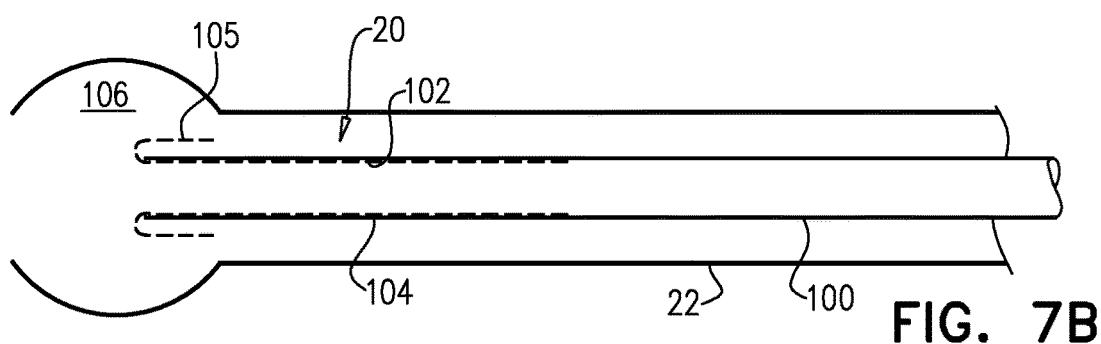
Figure 7C:
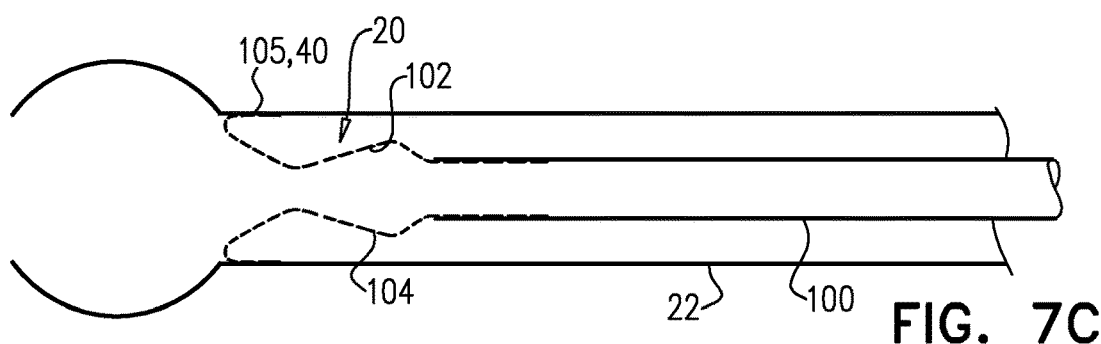
Figure 7D:
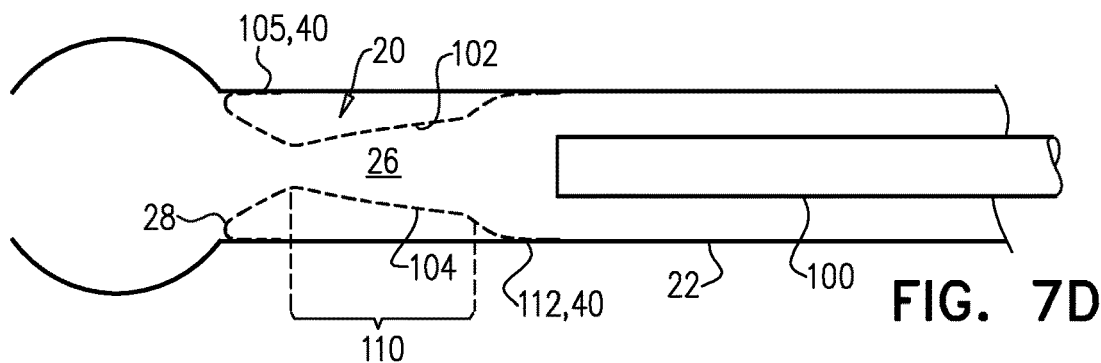

FIG. 7A shows device 20 in its constrained configuration inside the delivery device, FIG. 7D shows device 20 in its non-constrained configuration inside aorta 22, while FIGS. 7B and 7C show device 20 during the transition from its constrained to its non-constrained configuration. As may be observed by the transition from FIG. 7A to FIG. 7B, for some applications, upon being released from the delivery device, inner surface 102 at the upstream end of device 20 inverts, to form an inverted portion 105. For some applications, prior to this step, the distal end of the delivery device (i.e., the end of the delivery device that is inserted the furthest into the subject's body) is advanced to be adjacent to the aortic sinuses 106. Typically, at this location the aorta is slightly wider than locations within the ascending aorta that are further downstream. When the delivery device is retracted from the location adjacent to the aortic sinuses, the inner surface at the upstream end of device 20 has a wider space within which to invert, than if this step were to be performed at a location within the ascending aorta that is downstream of this location. Alternatively, this step may be performed at a location within the ascending aorta that is downstream of the aortic sinuses, and the inner surface at the upstream end of device 20 may have sufficient space within to invert by virtue of the difference between the diameter of the delivery device and the inner diameter of the aorta.

It is noted that, typically (as shown), the delivery device is inserted into the ascending aorta from a location that is superior to the ascending aorta. For example, the delivery device may be inserted into the subject's femoral artery and may then be advanced toward the ascending aorta via the descending aorta and the aortic arch. Or, the delivery device may be inserted via the subject's subclavian artery. For such applications, the upstream end of device 20 is typically released from the delivery device prior to the downstream end of device 20 being released from the delivery device. It is noted that for some of applications of device 20 described herein, the device may be inserted into the ascending aorta from a location that is inferior to the ascending aorta. For example, the device may be transapically inserted.

Referring now to FIGS. 7C and 7D, further retraction of the delivery device causes (a) the upstream end of the delivery device to radially expand such that inverted portion 105 of the inner surface contacts the inner wall of the aorta, thereby acting as the proximal portion of support structure 40, as described hereinabove, (b) a central portion 110 of the device to radially expand such that along the central portion of the device, the inner surface defines diverging portion 25 of conduit 26 that diverges in a direction from an upstream end of the conduit to a downstream end of the conduit, such that a cross-sectional area of the diverging portion of the conduit at its downstream end is greater than the cross-sectional area of the diverging portion of the conduit at its upstream end, and (c) the downstream end of the device to radially expand such that a downstream portion 112 of the outer surface at the contacts the inner wall of the aorta, thereby acting as the distal portion of support structure 40, as described hereinabove. The characteristics of the diverging conduit 26 are generally similar to those described hereinabove with reference to device 20.

As shown in FIG. 7D, once the delivery device is fully retracted, and device 20 has assumed its non-constrained configuration, the inverted portion of the inner surface at the upstream end of the device and the outer surface at the downstream end of the device anchor the device within the ascending aorta. The central portion of the device provides a diverging conduit, which functions as described hereinabove. As shown, the downstream end of the inner surface extends radially outward to the inner wall of the blood vessel, such that the distal end of the inner surface impedes blood flow around the outside of the distal end of the conduit. In addition, a portion of the inner surface between the inverted portion and the central portion of the inner surface acts as proximal outer surface 28 and is configured to impede antegrade blood flow around the outside of the proximal end of the conduit, as described hereinabove.

Figure 8A:
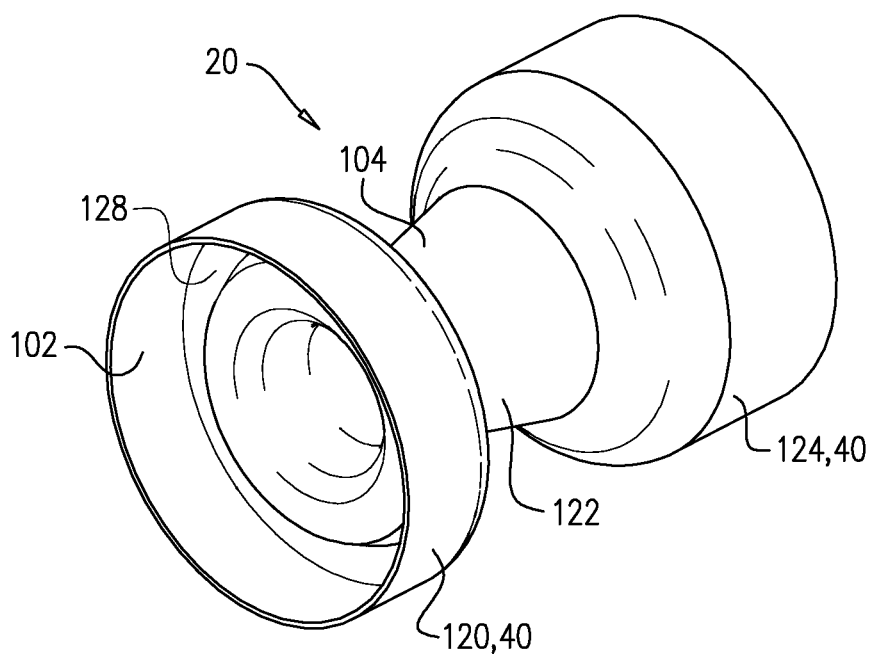
FIGS. 8A and 8B are schematic illustrations of a device for implanting inside a blood vessel of a subject, in accordance with some applications of the present invention.
Figure 8B:
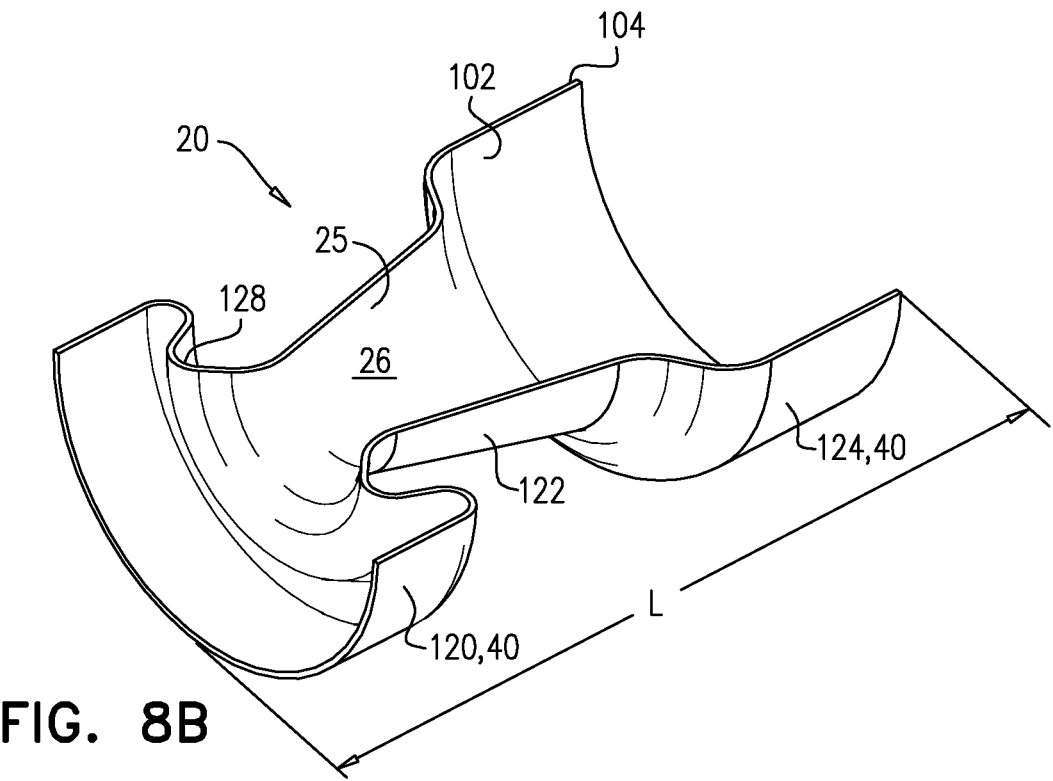

Reference is now made to FIGS. 8A and 8B, which are schematic illustrations of device 20 for implanting inside a blood vessel of a subject, in accordance with some applications of the present invention. FIG. 8A shows a three-dimensional view of the device, and FIG. 8B shows a cross-sectional view of the device, both FIGS. 8A and 8B showing the device in its non-constrained configuration. Device 20 as shown in FIGS. 8A and 8B is generally similar to device 20 as shown in FIGS. 6A and 6B, except for the differences described below. As described with reference to FIGS. 6A and 6B, for some applications, device 20 is formed from a single continuous portion of graft material. The graft material is typically formed from a combination of a metal or alloy frame (e.g., a stent made of stainless steel or nitinol) and fabric (such as expanded polytetrafluoroethylene (ePTFE) or woven polyester). For some applications, the frame of the stent graft material is a braided stent. For some applications, the braided stent provides flexibility to the device that facilitates insertion of the device via curved portions of the vasculature. For some applications, using a braided stent allows the device to be radially constrained to a narrower diameter than would be possible using a non-braided stent.

Typically, device 20 is inserted into the subject's aorta via a delivery device, such as catheter 100 (shown in FIGS. 7A, 7B, 7C, and 7D), in a generally similar manner to that described with reference to device 20 as shown in FIGS. 6A and 6B. While device 20 is disposed inside the delivery device, the delivery device constrains device 20 in a constrained configuration, in which device 20 defines a tube, having an inner surface 102 and an outer surface 104 (as shown in FIG. 7A). As noted above, since device 20 is formed from graft material, typically the tube includes folds on its surfaces, due to folding of the graft material. Moreover, the device does not necessarily define a precise cylindrical tube in this configuration. Rather, the device typically has a generally tubular shape in which the device defines inner surface 102 and outer surface 104. In order to implant device 20 inside the subject's ascending aorta, device 20 is released from the delivery device, e.g., by retracting the delivery device. Releasing the device from the delivery device causes device 20 to assume a non-constrained configuration, which is the configuration shown in FIGS. 8A and 8B. Upon being released from the delivery device, the upstream end of the device radially expands such that an upstream portion 120 of the outer surface of the device contacts the inner wall of the aorta, thereby acting as the proximal portion of outer support structure 40 described hereinabove. A central portion 122 of the device of the device radially expands such that along the central portion of the device, the inner surface defines diverging portion 25 of conduit 26 that diverges in a direction from a proximal end of the conduit to a distal end of the conduit, such that a cross-sectional area of the diverging portion of the conduit at its distal end is greater than the cross-sectional area of the diverging portion of the conduit at its proximal end. The characteristics of the diverging conduit 26 are generally similar to those described hereinabove with reference to device 20. The downstream end of the device radially expands such that a downstream portion 124 of the outer surface contacts the inner wall of the aorta, thereby acting as the distal portion of outer support structure 40 described hereinabove.

Typically, the upstream end of the device transitions from its constrained configuration to its non-constrained configuration by a portion of the device folding. For example, as shown the device may form a folded portion 128 that has a sinusoidal cross-sectional shape. Typically, due to the folded portion, along the longitudinal direction, there is partial overlap between upstream portion 120 of the outer surface of the device (which contacts the inner wall of the blood vessel), and the central portion of the device (which defines conduit 26). For some applications, the folded portion enhances sealing between the proximal end of the device and the aorta, by enhancing the radial force that the proximal end of the device exerts upon the inner wall of the aorta.

For some applications (not shown), folded portion 128 is such that the proximal end of conduit 26 extends proximally beyond the proximal end of upstream portion 120. For some applications (not shown), folded portion 128 is such that the upstream portion 120 extends distally such that it overlaps with most of (e.g., all of) central portion 122 of the device (which defines the diverging portion of conduit 26).

Once device 20 has assumed its non-constrained configuration, upstream portion 120 of the outer surface of the device (which contacts the inner wall of the blood vessel) and downstream portion 124 of the outer surface (which contacts the inner wall of the blood vessel) anchor the device within the ascending aorta. The central portion of the device provides a diverging conduit, which functions as described hereinabove. The downstream end of the inner surface extends radially outward to the inner wall of the blood vessel, such that the distal end of the inner surface impedes blood flow around the outside of the distal end of the conduit. In addition, folded portion 128 acts as proximal outer surface 28 and is configured to impede antegrade blood flow around the outside of the proximal end of the conduit.

For some applications, device 20 has a generally similar non-constrained configuration to that shown in FIGS. 8A and 8B, except that the device does not include folded portion 128. For some such applications, the device has an hourglass shape, the proximal (upstream) end of the device converging from upstream portion 120 to the beginning of the diverging portion of conduit 26. For some applications (not shown), the device includes an anchor (e.g., a ring, or a skirt) at its proximal (upstream end) that is configured to engage the subject's aortic sinus, to thereby anchor the device.

Figure 9:
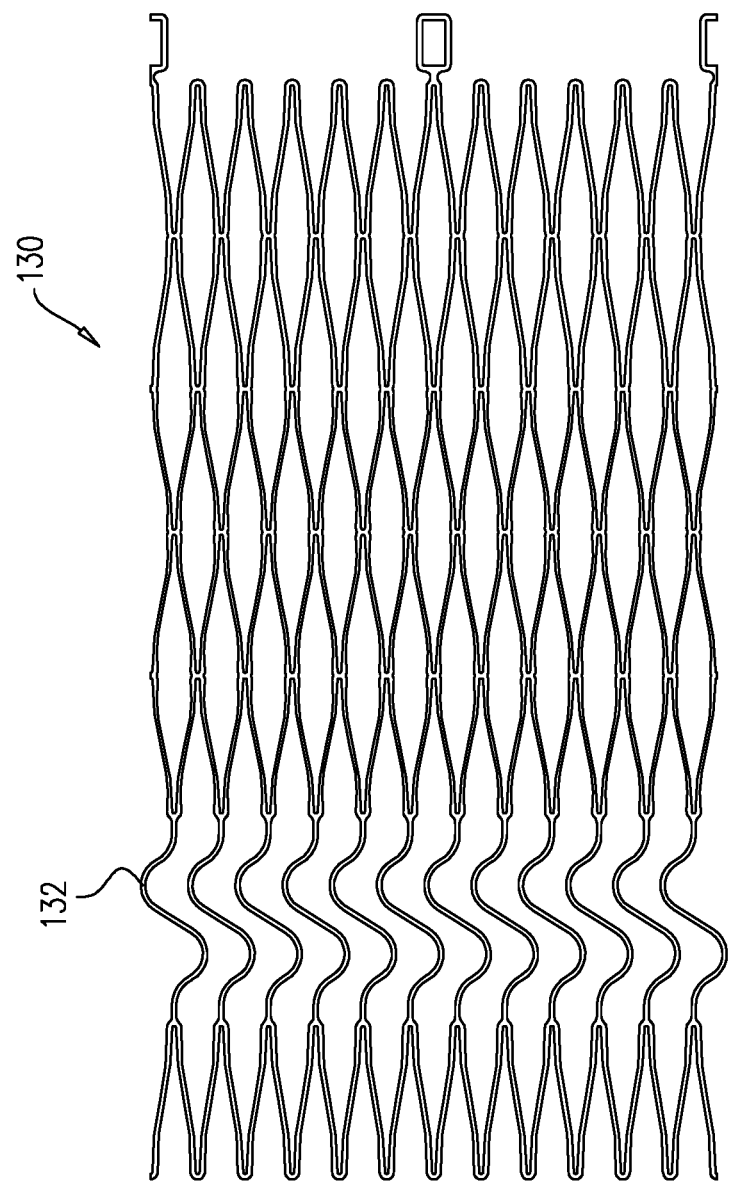
FIG. 9 is a schematic illustration of a flattened profile of a frame of the device of FIGS. 8A and 8B, in accordance with some applications of the present invention.

Reference is now made to FIG. 9 is a schematic illustration of a flattened profile of a frame 130 of device 20 of FIGS. 8A and 8B, in accordance with some applications of the present invention. As described hereinabove, for some applications, device 20 is formed from a single continuous portion of graft material. The graft material is typically formed from a combination of frame 130, which is typically a metal or an alloy (e.g., a stent made of stainless steel or nitinol) and fabric (such as expanded polytetrafluoroethylene (ePTFE) or woven polyester). The profile shown in FIG. 9 depicts (for illustrative purposes) how the frame of the device would appear if a longitudinal incision were to be made along the length of the frame at a given circumferential location of the frame, and the frame were to then be laid out flat upon a surface. As shown, for some applications, at the longitudinal location corresponding to folded portion 128, the frame defines sinusoidal struts 132. For some applications, the sinusoidal struts facilitate shape setting the frame of device 20 to include folded portion 128, such that the folded portion can encompass a smaller diameter relative if the folded portion were to be formed solely via the shape-setting process. For some applications, the folded portion can thereby be longer, such as to enhance sealing with respect to the aorta that is provided by the folded portion, as described hereinabove. For some applications, the folded portion encompassing a smaller diameter facilitates placement of the device closer to the orifice of the aortic valve.

With reference to device 20 as shown in FIGS. 6A-B and 8A-B, it is noted that since device 20 is shaped as a tube during insertion of the device via the delivery device, device 20 has a relatively narrow profile. As such, the delivery device (e.g., catheter 100) typically has a diameter of 16 Fr or less, e.g. 12 Fr or less. By contrast, if device 20 was configured to define overlapping layers in its constrained configuration (e.g., by inverted portion 105 being inverted, or folded portion 128 being folded, even in the device's constrained configuration) then the profile of the device would be greater, and the diameter of the delivery device would be greater.

With respect to device 20 as shown in FIGS. 6A-B and 8A-B, it is noted that dimensions of the device in its non-constrained configuration are typically as described hereinabove. Typically, length L of device 20 is greater than 20 mm (e.g., greater than 30 mm), and/or less than 70 mm (e.g., less than 60 mm), e.g., 20-70 mm, or 30-60 mm. Typically, the dimensions of diverging portion 25 of conduit 26 are generally similar to those described hereinabove. For some applications, the length of diverging portion 25 of conduit 26 (measured along the longitudinal axis of the device) is greater than 20 mm (e.g., greater than 30 mm), and/or less than 70 mm (e.g., less than 60 mm), e.g., 20-70 mm, or 30-60 mm, and length L of the device is greater than the length of diverging portion 25.

For the device as shown in FIGS. 6A and 6B, inverted portion 105 typically acts as the proximal end of the outer support structure, as described hereinabove with reference to FIG. 2A, for example. Downstream portion 112 of the outer surface acts as the distal end of the outer support structure. Therefore, typically (when the device in its non-constrained configuration), the ratio of the outer diameter of inverted portion 105 to the outer diameter of downstream portion 112 of the outer surface is greater than 3:4, and/or less than 4:3, e.g., between 3:4 and 4:3.

For the device as shown in FIGS. 8A and 8B, upstream portion 120 of the outer surface typically acts as the proximal end of the outer support structure, while downstream portion 124 of the outer surface acts as the distal end of the outer support structure, as described hereinabove with reference to FIG. 2A, for example. Therefore, typically (when the device in its non-constrained configuration), the ratio of the outer diameter of upstream portion 120 of the outer surface to the outer diameter of downstream portion 124 of the outer surface is greater than 3:4, and/or less than 4:3, e.g., between 3:4 and 4:3.

As described with reference to FIG. 2A, typically, the maximum outer diameter of the device (i.e., the outer diameter of the device at the location along the length of the device at which the outer diameter is at its maximum) is greater than 18 mm (e.g., greater than 25 mm), and/or less than 45 mm (e.g., less than 35 mm), e.g., 18-45 mm, or 25-35 mm.

It is noted that, although device 20 is generally described herein as being implanted in the subject's aorta (e.g., ascending aorta), the scope of the present invention includes placing device 20 inside a longitudinal portion of any blood vessel of a subject, such that the device causes blood to flow in an antegrade direction through conduit 26, and such that, within the longitudinal portion in which the device is placed, blood flow via any flow-path other than through the conduit is prevented by the deployment of the device within the portion.

The terms "proximal" and "distal" are generally used in the present application to refer to the location of the respective elements in the aorta with respect to the aortic valve. That is, the term "proximal" refers to an element that is "upstream" and closer to the aortic valve, and the term "distal" refers to an element that is "downstream" and further from the aortic valve. Thus, the term "proximal" is used synonymously with the term "upstream" and the term "distal" is used synonymously with the term "downstream." In cases in which the device is placed in a different position within the subject's body, the terms "proximal" and "distal" are to be understood with respect to the direction of blood flow, a location that is relatively upstream being considered "proximal" and a location that is relatively downstream being considered "distal." It is noted that when used with reference to catheter 100, the term "distal" is used to refer to the end of the catheter that is inserted the furthest into the subject's body.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a delivery device, comprising:
an implantable device having a proximal end and a distal end, the implantable device being configured:
to be inserted into an ascending aorta of a subject while the implantable device is disposed inside the delivery device and is constrained in a constrained configuration by the delivery device,
to assume a non-constrained configuration inside a longitudinal portion of the ascending aorta by being released from the delivery device, the implantable device being configured such that when disposed in the non-constrained configuration inside the longitudinal portion of the ascending aorta:
a proximal portion of the implantable device contacts an inner wall of the ascending aorta, such as to anchor the proximal end of the implantable device with respect to the ascending aorta,
along a central portion of the implantable device, an inner surface of the implantable device defines a conduit extending through the implantable device, the conduit comprising a diverging portion that diverges in a direction from a proximal end of the conduit to a distal end of the conduit, such that a cross-sectional area of the diverging portion of the conduit at its distal end is greater than the cross-sectional area of the diverging portion of conduit at its proximal end, the diverging portion being configured to reduce pressure loss of blood flowing through the conduit, relative to pressure loss of blood flowing through the longitudinal portion of the ascending aorta in an absence of the device, by reducing an area of flow separation,
the proximal end of the conduit being configured to be placed within the ascending aorta such that when an aortic valve of the subject is in an open state, the proximal end of the conduit is disposed within 25 mm of a tip of the aortic valve,
a distal portion of the implantable device contacts the inner wall of the ascending aorta, such as to anchor the distal end of the implantable device with respect to the ascending aorta, and
the implantable device defines a folded portion radially between the proximal portion of the implantable device and the central portion of the implantable device, such that along a longitudinal direction of the implantable device, there is partial overlap between the proximal portion of the implantable device and the central portion of the implantable device.

2. The apparatus according to claim 1, wherein the implantable device is configured to define the folded portion by defining a folded portion that has a sinusoidal cross-sectional shape.

3. The apparatus according to claim 1, wherein the implantable device does not include a prosthetic valve.

4. The apparatus according to claim 1, wherein, when in the non-constrained configuration inside the ascending aorta, the implantable device is configured to define, at a region at its distal end, a surface extending radially outward, around a full circumference of the conduit, from the conduit to the inner wall of the ascending aorta.

5. The apparatus according to claim 1, wherein the implantable device is made of a single continuous piece of stent graft material.

6. The apparatus according to claim 1, wherein the implantable device is configured such that, when the implantable device is in the non-constrained configuration within the ascending aorta, the diverging portion of the conduit has a length of more than 20 mm.

7. The apparatus according to claim 6, wherein the implantable device is configured such that, when the implantable device is in the non-constrained within the ascending aorta, the length of the diverging portion of the conduit is less than 70 mm.

8. The apparatus according to claim 1, wherein the implantable device is configured such that, when the implantable device is in the non-constrained configuration inside the ascending aorta, a ratio between a diameter of the conduit at the distal end of the diverging portion of the conduit and a diameter of the conduit at the proximal end of the diverging portion of the conduit is less than 4:3.

9. The apparatus according to claim 1, wherein the implantable device is configured such that, when the implantable device is in the non-constrained configuration inside the ascending aorta, the ratio between the diameter of the conduit at the distal end of the diverging portion of the conduit and the diameter of the conduit at the proximal end of the diverging portion of the conduit is more than 7:6.

10. The apparatus according to claim 1, wherein, when in the non-constrained configuration inside the ascending aorta, the implantable device is configured to impede blood flow through the longitudinal portion of the ascending aorta in which the implantable device is placed, via any flow path other than through the conduit, to less than 20 percent of total blood flow through the longitudinal portion of the ascending aorta.

11. The apparatus according to claim 10, wherein, when in the non-constrained configuration inside the ascending aorta, the implantable device is configured to impede blood flow through the longitudinal portion of the ascending aorta in which the implantable device is placed such that there is no blood flow through the longitudinal portion of the ascending aorta, via any flow path other than through the conduit.

12. A method comprising:
inserting an implantable device into an ascending aorta of a subject while the implantable device is disposed inside a delivery device and is constrained in a constrained configuration by the delivery device; and
releasing the implantable device from the delivery device into the ascending aorta, thereby causing the implantable device to assume a non-constrained configuration within a longitudinal portion of the ascending aorta, by:
an upstream end of the implantable device radially expanding such that an upstream portion of the implantable device contacts an inner wall of the ascending aorta,
a central portion of the implantable device radially expanding such that the central portion of the implantable device defines a conduit extending through the implantable device, the conduit comprising a diverging portion that diverges in a direction from an upstream end of the conduit to a downstream end of the conduit, such that a cross-sectional area of the diverging portion of the conduit at its downstream end is greater than the cross-sectional area of the diverging portion of the conduit at its upstream end, the diverging portion being configured to reduce pressure loss of blood flowing through the conduit, relative to pressure loss of blood flowing through the longitudinal portion of the ascending aorta in an absence of the device, by reducing an area of flow separation,
the proximal end of the conduit being placed within the longitudinal portion of the ascending aorta such that when an aortic valve of the subject is in an open state, the proximal end of the conduit is disposed within 25 mm of a tip of the aortic valve,
a downstream end of the implantable device radially expanding such that a downstream portion of the implantable device contacts an inner wall of the ascending aorta, such as to anchor the downstream end of the implantable device with respect to the ascending aorta, and the implantable device forming a folded portion radially between the upstream portion of the implantable device and the central portion of the implantable device, such that along a longitudinal direction of the implantable device, there is partial overlap between the upstream portion of the implantable device and the central portion of the implantable device.

13. The method according to claim 12, wherein causing the implantable device to assume the non-constrained configuration comprises causing the implantable device to form the folded portion by forming a folded portion that has a sinusoidal cross-sectional shape.

14. The method according to claim 12, wherein the implantable device does not include a prosthetic valve, and wherein inserting the implantable device into the ascending aorta does not include inserting a prosthetic valve into the ascending aorta.

15. The method according to claim 12, wherein releasing the implantable device from the delivery device into the ascending aorta, comprises causing the implantable device to assume a non-constrained configuration in which the implantable device defines, at a region at its downstream end, a surface extending radially outward, around a full circumference of the conduit, from the conduit to the inner wall of the ascending aorta.

16. The method according to claim 12, wherein the implantable device includes an implantable device made of a single continuous piece of stent graft material.

17. The method according to claim 12, wherein releasing the implantable device from the delivery device into the ascending aorta, comprises causing the implantable device to assume a non-constrained configuration in which the diverging portion of the conduit has a length of more than 20 mm.

18. The method according to claim 17, wherein releasing the implantable device from the delivery device into the ascending aorta, comprises causing the implantable device to assume a non-constrained configuration in which the length of the diverging portion of the conduit is less than 70 mm.

19. The method according to claim 12, wherein releasing the implantable device from the delivery device into the ascending aorta, comprises causing the implantable device to assume a non-constrained configuration in which a ratio between a diameter of the conduit at the downstream end of the diverging portion of the conduit and a diameter of the conduit at the upstream end of the diverging portion of the conduit is less than 4:3.

20. The method according to claim 12, wherein releasing the implantable device from the delivery device into the ascending aorta, comprises causing the implantable device to assume a non-constrained configuration in which the ratio between the diameter of the conduit at the downstream end of the diverging portion of the conduit and the diameter of the conduit at the upstream end of the diverging portion of the conduit is more than 7:6.

21. The method according to claim 12, wherein releasing the implantable device from the delivery device into the ascending aorta, comprises causing the implantable device to assume a non-constrained configuration in which the implantable device impedes blood flow through the longitudinal portion of the ascending aorta, via any flow path other than through the conduit, to less than 20 percent of total blood flow through the longitudinal portion of the ascending aorta.

22. The method according to claim 21, wherein releasing the implantable device from the delivery device into the ascending aorta, comprises causing the implantable device to assume a non-constrained configuration in which the implantable device impedes blood flow through the longitudinal portion of the ascending aorta such that there is no blood flow through the longitudinal portion of the ascending aorta, via any flow path other than through the conduit.

* * * * *